US008829202B2

(12) United States Patent
Ikeda et al.

(10) Patent No.: US 8,829,202 B2
(45) Date of Patent: Sep. 9, 2014

(54) CONDENSED POLYCYCLIC AROMATIC COMPOUND, AROMATIC POLYMER, AND METHOD FOR SYNTHESIZING AROMATIC COMPOUND

(75) Inventors: Yoshinori Ikeda, Hino (JP); Azusa Kohno, Hino (JP); Takashi Shiro, Hino (JP); Kazuo Takimiya, Higashihiroshima (JP)

(73) Assignee: Teijin Limited, Osaka (JP)

( * ) Notice: Subject to any disclaimer, the term of this patent is extended or adjusted under 35 U.S.C. 154(b) by 0 days.

(21) Appl. No.: 14/237,103

(22) PCT Filed: Aug. 3, 2012

(86) PCT No.: PCT/JP2012/069896
§ 371 (c)(1),
(2), (4) Date: Feb. 4, 2014

(87) PCT Pub. No.: WO2013/021953
PCT Pub. Date: Feb. 14, 2013

(65) Prior Publication Data
US 2014/0187792 A1 Jul. 3, 2014

(30) Foreign Application Priority Data

| Aug. 5, 2011 | (JP) | 2011-172296 |
| Aug. 5, 2011 | (JP) | 2011-172301 |
| Oct. 6, 2011 | (JP) | 2011-222355 |
| Aug. 2, 2012 | (JP) | 2012-171821 |
| Aug. 2, 2012 | (JP) | 2012-171873 |
| Aug. 2, 2012 | (JP) | 2012-171915 |

(51) Int. Cl.
*C07D 495/14* (2006.01)
*C07D 495/18* (2006.01)
*C07D 495/04* (2006.01)
*C07F 7/08* (2006.01)

(52) U.S. Cl.
CPC ............ *C07D 495/04* (2013.01); *C07F 7/0812* (2013.01); *C07D 495/18* (2013.01)
USPC ............................................. 548/417; 549/31

(58) Field of Classification Search
None
See application file for complete search history.

(56) References Cited

U.S. PATENT DOCUMENTS

| 3,346,612 | A | 10/1967 | Hansen |
| 2009/0001357 | A1 | 1/2009 | Takimiya et al. |
| 2009/0043113 | A1 | 2/2009 | Park et al. |
| 2010/0065826 | A1 | 3/2010 | Takimiya et al. |

FOREIGN PATENT DOCUMENTS

| DE | 32 25 386 A1 | 1/1984 |
| JP | 2002-526527 A | 8/2002 |
| JP | 2006-089413 A | 4/2006 |
| JP | 2008-10541 A | 1/2008 |
| JP | 2008-290963 A | 12/2008 |
| JP | 2009-62302 A | 3/2009 |
| JP | 2009-124064 A | 6/2009 |
| JP | 2009-533444 A | 9/2009 |
| JP | 2010-540545 A | 12/2010 |
| WO | 2000/020389 A1 | 4/2000 |
| WO | 2006/077888 A1 | 7/2006 |
| WO | 2007/120655 A2 | 10/2007 |
| WO | 2008/050726 A1 | 2/2008 |
| WO | 2009/042542 A1 | 4/2009 |
| WO | 2011/024804 A1 | 3/2011 |

OTHER PUBLICATIONS

Kazuki Niimi, et al., "General Synthesis of Dinaphtho-[2,3-b:2',3'-f]thieno[3,2-b]thiophene (DNTT) Derivatives", Organic Letters, 2011, pp. 3430-3433, vol. 13, No. 13.
Tatsuya Yamamoto, et al., "Largely Pi-Extended Thienoacenes with Internal Thieno[3,2-b]thiophene Substructures: Synthesis, Characterization, and Organic Field-Effect Transistor Applications", Organic Letters, 2012, pp. 4914-4917, vol. 14, No. 18.
Tatsuya Yamamoto, et al., "Facile Synthesis of highly Pi-Extended Heteroarenes, Dinaphtho[2,3- b:2',3'-f]chalcogenopheno[3,2-b]chalcogenophenes, and Their Application to Field-Effect Transistors", J. Am. Chem. Soc., 2007, pp. 2224-2225, vol. 129.
Hidemitsu Uno, et al., "Photo precursor for pentacene", Tetrahedron Letters, 2005, pp. 1981-1983, vol. 46.
Yu-Man Wang, et al., "Synthesis, characterization, and reactions of 6,13-disubstituted 2,3,9,10-tetrakis(trimethylsilyl)pentacene derivatives", Tetrahedron, 2007, pp. 8586-8597, vol. 63.
Yingping Zou, et al., "New cyano-substituted copolymers containing biphenylenevinylene and bithienylenevinylene units: synthesis, optical, and electrochemical properties", J. Mater. Sci., 2009, pp. 4174-4180, vol. 44.
Yang Ni, et al., "Zirconium-Mediated Coupling Reaction for Synthesis of Substituted Thiophene-Fused Acenes", Organic Letters, 2009, pp. 3702-3705, vol. 11, No. 16.
Japanese Office Action of JP 2012-171831 dated Apr. 16, 2013.
Japanese Office Action of JP 2012-171831 dated Jan. 15, 2013.
International Search Report for PCT/JP2012/069896 dated Nov. 13, 2012.
Jikken Kagaku Kouza, "Synthesis of Organic Compound—Hydrocarbon and Halide", Experimental Chemical Course, Feb. 20, 2004, pp. 379, vol. 13.

*Primary Examiner* — Michael Barker
(74) *Attorney, Agent, or Firm* — Sughrue Mion, PLLC

(57) ABSTRACT

Provided is a condensed polycyclic aromatic compound that can be used as a precursor for synthesizing a condensed polycyclic aromatic compound having relatively high solubility. Also provided is a method for synthesizing and using such a novel condensed polycyclic aromatic compound. The condensed polycyclic aromatic compound is represented by formula (II): (II) (where $X_1$ and $X_2$ are each independently selected from the group consisting of a hydrogen atom, halogen atom, alkyl group, and the like, but at least one of $X_1$ and $X_2$ is a halogen atom; B is a condensed ring having at least one benzene ring moiety; each Y is independently selected from chalcogens; and $A_1$ through $A_4$ are each independently selected from the group consisting of hydrogen atoms, halogen atoms, alkyl groups, and the like and two adjacent atoms or groups can bond together to form an aromatic group).

16 Claims, 2 Drawing Sheets

CONDENSED POLYCYCLIC AROMATIC COMPOUND, AROMATIC POLYMER, AND METHOD FOR SYNTHESIZING AROMATIC COMPOUND

CROSS REFERENCE TO RELATED APPLICATIONS

This application is a National Stage of International Application No. PCT/JP2012/069896 filed Aug. 3, 2012, claiming priority based on Japanese Patent Application Nos. 2011-172296 and 2011-172301 filed Aug. 5, 2011, 2011-222355 filed Oct. 6, 2011, 2012-171821, 2012-171873, and 2012-171915 filed Aug. 2, 2012, the contents of all of which are incorporated herein by reference in their entirety.

TECHNICAL FIELD

First and Second Aspects of the Present Invention

First and second aspects of the present invention relate to a novel condensed polycyclic aromatic compound. Also, the first and second aspects of the present invention relate to synthesis and use methods of the novel condensed polycyclic aromatic compound.

Third Aspect of the Present Invention

A third aspect of the present invention relates to a novel aromatic polymer. Also, the present invention relates to synthesis and use methods of the novel aromatic polymer.

Fourth and Fifth Aspects of the Present Invention

Fourth and fifth aspects of the present invention relate to a method for synthesizing an aromatic compound. More specifically, the present invention relates to an intermediate aromatic compound for the synthesis of [1]benzothieno[3,2-b][1]benzothiophene (hereinafter, referred to as "DNTT" or "dinaphthothienothiophene") or a derivative thereof, a synthesis method of the intermediate aromatic compound, and a method for synthesizing DNTT or a derivative thereof, including the synthesis method above.

[Chem. 1]

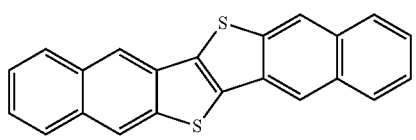

Dinaphthothienothiophene (DNTT)

BACKGROUND ART

First to Third Aspects of the Present Invention

Various studies are being made on use of an organic semiconductor compound in an organic thin-film transistor (TFT), an organic carrier transport layer, an organic semiconductor layer for an organic light-emitting device, or the like. In particular, a thin-film transistor having an organic semiconductor layer composed of an organic semiconductor compound is a low-cost lightweight device, and expected to substitute for the current silicon-based transistor. The organic semiconductor layer is also expected to be applied to a smart tag, a lightweight display and the like, by utilizing the advantages peculiar to an organic material, such as lightness and flexibility.

Accordingly, many studies are being made on an organic semiconductor compound to form an organic semiconductor layer (Patent Documents 1 to 5 and Non-Patent Documents 1 to 3).

Among these organic semiconductor compounds, a condensed polycyclic aromatic compound, and particularly dinaphthothienothiophene (DNTT), a substitution product thereof, or a condensed polycyclic aromatic compound having a similar structure, has been found to be preferable in terms of semiconductor characteristics such as stability of the material and mobility of the carrier.

However, the condensed polycyclic aromatic compound has high aromaticity and high crystallinity and in turn, exhibits very low solubility in an organic solvent or the like, making it difficult to use the compound in a coating method. For this reason, in the case of obtaining an organic semiconductor film by using a condensed polycyclic aromatic compound, it is a general practice to obtain an organic semiconductor thin film composed of a condensed polycyclic aromatic compound by a vapor deposition method.

Alternatively, DNTT exhibits slight solubility for an organic solvent because of a small number of fused rings, but still falls short of achieving sufficient solubility for its industrial use in a solution method (Patent Document 4).

In addition, a low-molecular organic semiconductor compound having sufficient solubility for use in a solution method, such as dioctylbenzothienobenzothiophene (C8-BTBT), is known. However, in the case of using such a low-molecular organic semiconductor compound, the size of crystal precipitated in the solution process is greatly varied and in turn, the characteristics of the obtained semiconductor film tend to become non-uniform. Therefore, when a thin-film transistor (TFT) array is formed of a device using such an organic semiconductor film, variation in the characteristics may occur among devices. Furthermore, in the case of using the above-described low-molecular organic semiconductor compound in a solution method, the viscosity of the solution is low, and therefore it is not easy to obtain an organic semiconductor film having a sufficient thickness and to form a semiconductor film on a hydrophobic surface.

Incidentally, in order to obtain an organic semiconductor thin film by using a condensed polycyclic aromatic compound such as DNTT in a coating method, it has been also proposed to use a precursor having high solubility, and producing such a condensed polycyclic aromatic compound by undergoing decomposition (Patent Document 5, Non-Patent Documents 2 and 3).

Fourth and Fifth Aspects of the Present Invention

With respect to the synthesis route of DNTT, the following conventional synthesis route (1) is known as a promising candidate therefor (Patent Document 2).

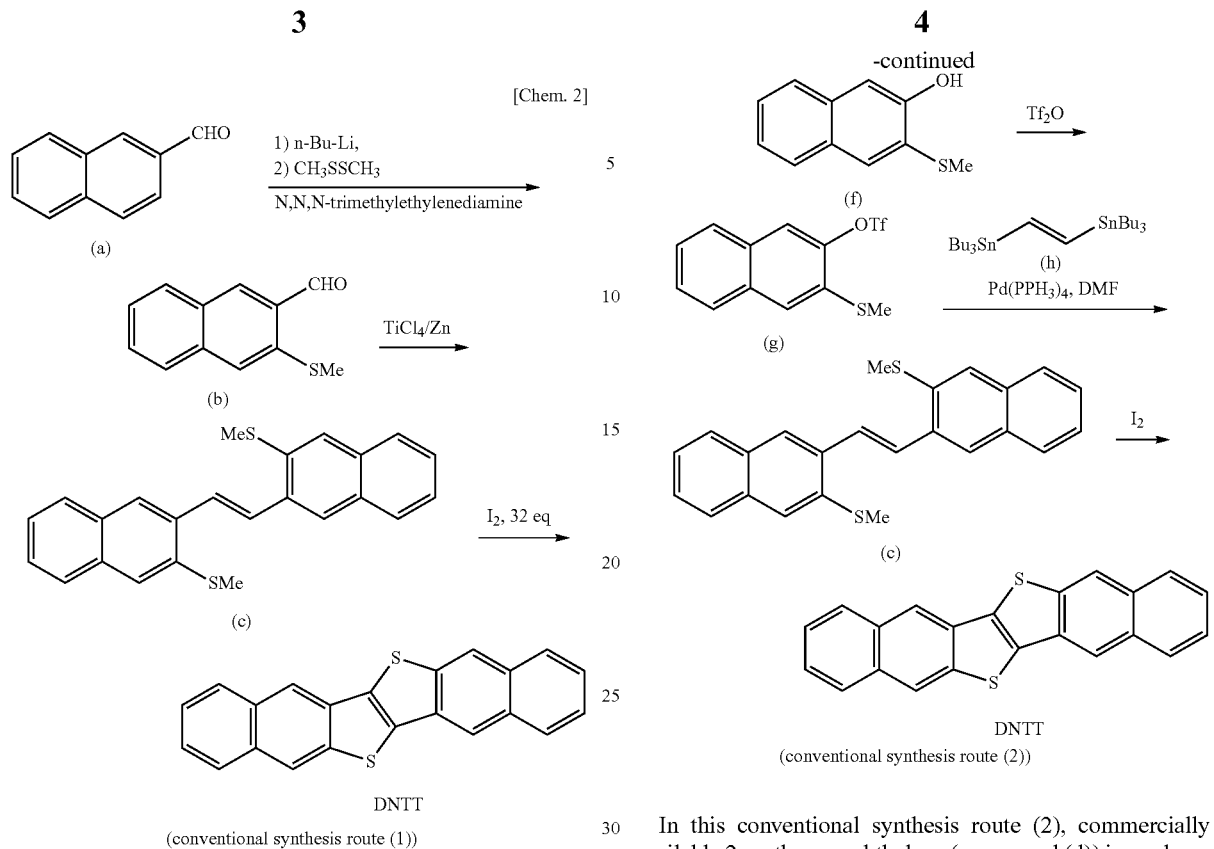

DNTT
(conventional synthesis route (1))

However, regarding this conventional synthesis route (1), in the step of synthesizing 3-methylthio-2-naphthaldehyde (formula (b)) from 2-naphthaldehyde (formula (a)), a byproduct in which a methylthio group is introduced into the 1- or 4-position is produced in addition to the target compound in which a methylthio group (-SMe) is introduced into the 3-position (formula (b)). Accordingly, the yield of the target compound (formula (b)) in this step is relatively low, and an additional purification treatment using a large amount of solvent, such as chromatograph separation and recrystallization, is required so as to remove the byproduct.

To cope with this problem, a method for synthesizing DNTT without synthesizing 3-methylthio-2-naphthaldehyde (formula (b)) from 2-naphthaldehyde (formula (a)) has been studied. For example, the following conventional synthesis route (2) has been proposed as such a method (Non-Patent Document 4).

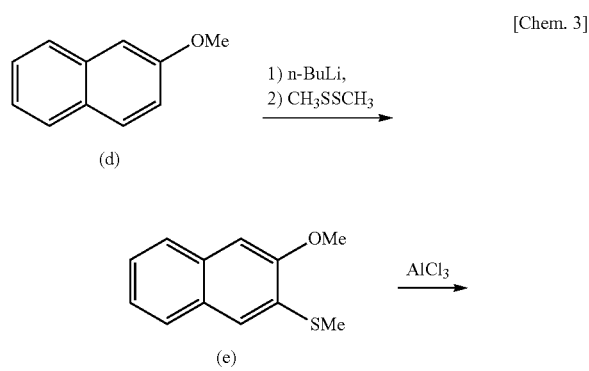

DNTT
(conventional synthesis route (2))

In this conventional synthesis route (2), commercially available 2-methoxynaphthalene (compound (d)) is used as a starting material so as to selectively introduce a methylthio group into the 3-position, whereby a high yield of 3-methylthio-2-methoxynaphthalene (formula (e)) is obtained. It is reported that the conventional synthesis route (2) requires a five-step reaction, but DNTT is obtained in a high yield of 79%.

In the conventional synthesis route (2), trans-1,2-bis(tributylstanyl)ethane (formula (h)) that is an organic tin coupling agent is required so as to obtain trans-1,2-bis(3-methylthionaphthalen-2-yl)ethane (formula (c)) by dimerizing 3-methylthio-2-triflatenaphthalene (formula (g)). However, since a relatively complicated reaction is necessary for synthesizing this organic tin coupling agent (Non-Patent Document 5), and in addition, since tin is used as a raw material, the organic tin coupling agent above is expensive (Wako Pure Chemical Industries, Ltd., 30,000 yen/5 g). Furthermore, 1 mol of the organic tin coupling above must be used for the synthesis of 1 mol of DNTT, and use of this coupling agent increases the synthesis cost of the conventional synthesis route (2).

RELATED ART

Patent Document

[Patent Document 1] JP-A-2006-89413
[Patent Document 2] JP-A-2008-290963
[Patent Document 3] WO2006/077888
[Patent Document 4] WO2008/050726
[Patent Document 5] WO2011/024804

Non-Patent Document

[Non-Patent Document 1] "Facile Synthesis of Highly π-Extended Heteroarenes, Dinaphtho[2,3-b:2',3'-f]chalcogenopheno[3,2-b]chalcogenophenes, and Their Application to Field-Effect Transistors", Tatsuya Yamamoto, and Kazuo Takimiya, J. Am. Chem. Soc., 2007, 129 (8), pp. 2224-2225

[Non-Patent Document 2] H. Uno et al., Photoprecursor for pentacene, Tetrahedron Letters, 2005, Vol. 46, No. 12, PP. 1981-1983

[Non-Patent Document 3] WANG, Y. et al., "Synthesis, characterization, and reactions of 6,13-disubstituted 2,3,9,10-tetrakis(trimethylsilyl)pentacene derivatives", Tetrahedron, 2007, Vol. 63, No. 35, pp. 8586-8597

[Non-Patent Document 4] Kazuki Niimi, et al., "General Synthesis of Dinaphtho[2,3-b:2',3'-f]thieno[3,2-b]thiophene (DNTT) Derivatives", Organic Letters (2011), 13 (13), pp. 3430-3433

[Non-Patent Document 5] ZOU Yingping et al., "New cyano-substituted copolymers containing biphenylenevinylene and bithienylenevinylene units: synthesis, optical, and electrochemical properties", J. Mater. Sci. 2009, 44, 4174-4180

SUMMARY OF THE INVENTION

Problems to be Solved by the Invention

First to Third Aspects of the Present Invention

As described above, DNTT exhibits slight solubility for an organic solvent because of a small number of fused rings, but still falls short of achieving sufficient solubility for its industrial use in a solution method (Patent Document 4).

Also, in the case where a low-molecular organic semiconductor compound having sufficient solubility is used in a solution method, there is a problem that variation in the characteristics occurs among devices using the obtained organic semiconductor film. Furthermore, in the case of using the above-described low-molecular organic semiconductor compound in a solution method, the viscosity of the solution is low, and therefore it is disadvantageously not easy to obtain an organic semiconductor film having a sufficient thickness and to form a semiconductor film on a hydrophobic surface.

Accordingly, the first and second aspects of the present invention provide a condensed polycyclic aromatic compound having a relatively high solubility, and synthesis and use methods of such a novel condensed polycyclic aromatic compound. Also, the third aspect of the present invention provides an aromatic polymer capable of at least partially solving the above-described problem, and synthesis and use methods of such a novel aromatic polymer.

Fourth and Fifth Aspects of the Present Invention

The present invention provides a novel method for synthesizing DNTT or a derivative thereof, which is free from the above-described problems in the conventional synthesis routes, and particularly a novel synthesis method of DNTT or a derivative thereof, in which an expensive raw material such as organic tin coupling agent is not required. Also, the present invention provides an intermediate aromatic compound for the novel synthesis method, and a synthesis method of the intermediate aromatic compound.

Means to Solve the Problems

First Aspect of the Present Invention

The inventors of the present invention have found that, by introducing a substituent into an aromatic ring adjacent to a central heterocyclic moiety of a condensed polycyclic aromatic compound having a similar structure to DNTT, the solubility of the condensed polycyclic aromatic compound is improved. The first aspect of the present invention has been achieved based on this finding.

The condensed polycyclic aromatic compound of the first aspect of the present invention is represented by the following formula (I):

[Chem. 4]

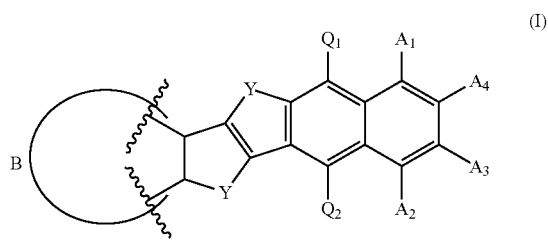

(wherein each of $Q_1$ and $Q_2$ is independently selected from the group consisting of a hydrogen atom, a halogen atom, an alkyl group and the like, and at least one of $Q_1$ and $Q_2$ is a group other than a hydrogen atom and a halogen atom;

B is a substituted or unsubstituted condensed ring having at least one benzene ring moiety;

each Y is independently selected from chalcogens; and each of $A_1$ to $A_4$ is independently selected from the group consisting of a hydrogen atom, a halogen atom, an alkyl group and the like, and two adjacent members may combine with each other to form an aromatic group).

The condensed polycyclic aromatic compound represented by formula (I) can be used as an organic semiconductor compound.

Also, the condensed polycyclic aromatic compound represented by formula (I) can have a relatively high solubility by virtue of a substituent (Q) on the benzene ring adjacent to the condensed heterocyclic ring in the central part. This may be attributable to the decreased crystallinity of the compound, increased the polarity of the compound as a whole due to the polarity of the substituent, or the like, which is caused by the presence of a substituent on the benzene ring adjacent to the condensed heterocyclic ring in the central part, i.e. by the presence of a substituent at a position close to the center of the condensed polycyclic aromatic compound.

Incidentally, the formula of Patent Document 4 encompasses DNTT of which hydrogen of the condensed benzene ring is substituted for. However, Document 4 merely discloses DNTT substituted at a position most distant from the condensed heterocyclic ring in the central part, and does not specifically disclose the embodiment wherein a benzene ring adjacent to the condensed heterocyclic ring in the central part is substituted. In addition, Patent Document 4 does not disclose a specific method for synthesizing DNTT of which a benzene ring adjacent to the condensed heterocyclic ring in the central part is substituted.

The first aspect of the present invention also relates to a solution, an organic semiconductor film, an organic semiconductor device and the like, each using the condensed polycyclic aromatic compound of the first aspect of the present invention.

Second Aspect of the Present Invention

The inventors of the present invention have found that the condensed polycyclic aromatic compound of the first aspect of the present invention can be easily synthesized by using a specific condensed polycyclic aromatic compound. The second aspect of the present invention has been achieved based on this finding.

The condensed polycyclic aromatic compound of the second aspect of the present invention is represented by the following formula (II):

[Chem. 5]

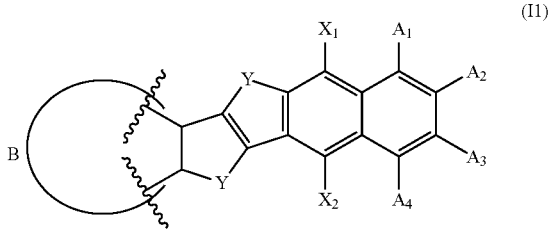

(II)

(wherein each of $X_1$ and $X_2$ is independently selected from the group consisting of a hydrogen atom, a halogen atom, an alkyl group and the like, and at least one of $X_1$ and $X_2$ is a halogen atom;

B is a condensed ring having at least one benzene ring moiety;

each Y is independently selected from chalcogens; and each of $A_1$ to $A_4$ is independently selected from the group consisting of a hydrogen atom, a halogen atom, an alkyl group and the like, and two adjacent members may combine with each other to form an aromatic group).

The condensed polycyclic aromatic compound of the second aspect of the present invention can be used as a precursor for the synthesis of the condensed polycyclic aromatic compound of the first aspect of the present invention. Specifically, according to the condensed polycyclic aromatic compound of the second aspect of the present invention, the condensed polycyclic aromatic compound of the first aspect of the present invention can be synthesized by various coupling methods using an aromatic halide, e.g. Mizoroki-Heck reaction, Negishi coupling, Migita-Kosugi-Stille coupling, Sonogashira coupling, Suzuki-Miyaura coupling, Buchwald-Hartwig reaction or Kumada-Tamao-Corriu coupling.

Also, the condensed polycyclic aromatic compound represented by formula (II) can have relatively large solubility by virtue of a halogen atom (X) on a benzene ring adjacent to the condensed heterocyclic ring in the central part. This may be attributable the decreased crystallinity of the compound, leading to high solubility, the increased polarity of the compound as a whole due to the polarity of the halogen group, or the like, which is caused by the presence of a halogen group on the benzene ring adjacent to the condensed heterocyclic ring in the central part, i.e. by the presence of a halogen group at a position close to the center of the condensed polycyclic aromatic compound.

The second aspect of the present invention also relates to a synthesis method, a use method and the like of the condensed polycyclic aromatic compound of the second aspect of the present invention.

Third Aspect of the Present Invention

The inventors of the present invention have found that the above-described problem can be at least partially solved by an aromatic polymer having two or more condensed polycyclic aromatic moieties having a similar structure to DNTT. The present invention has been achieved based on this finding.

The aromatic polymer of the present invention has two or more condensed polycyclic aromatic moieties represented by the following formula (IV):

[Chem. 6]

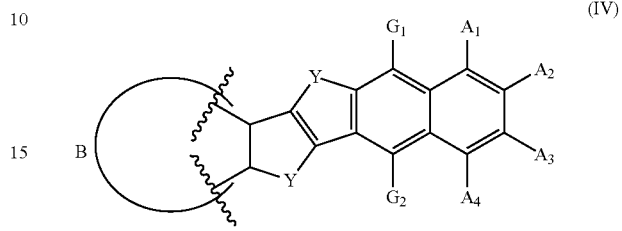

(IV)

(wherein each of $G_1$ and $G_2$ is independently selected from the group consisting of a bond, a hydrogen atom, a halogen atom, an alkyl group and the like, and at least one of $G_1$ and $G_2$ is a bond;

B is a condensed ring having at least one benzene ring moiety;

each Y is independently selected from chalcogens; and each of $A_1$ to $A_4$ is independently selected from the group consisting of a hydrogen atom, a halogen atom, an alkyl group and the like, and two adjacent members may combine with each other to form an aromatic group).

In the aromatic polymer of the present invention, the condensed polycyclic aromatic moiety can provide relatively large solubility by virtue of a bond or the like on a benzene ring adjacent to the condensed heterocyclic ring in the central part. This may be attributable to the decreased crystallinity of the moiety, leading to high solubility, the increased polarity of the moiety due to the polarity of the bond, or the like, which is caused by the presence of a bond or the like on the benzene ring adjacent to the condensed heterocyclic ring in the central part of the condensed polycyclic aromatic moiety, i.e. by the presence of a bond or the like at a position close to the center of the condensed polycyclic aromatic compound.

Incidentally, the formula of Patent Document 4 encompasses DNTT of which hydrogen of the condensed benzene ring is substituted for. However, Document 4 merely discloses DNTT substituted at a position most distant from the condensed heterocyclic ring in the central part, and does not specifically disclose the embodiment where a benzene ring adjacent to the condensed heterocyclic ring in the central part is substituted. In addition, Patent Document 4 does not disclose a specific method for synthesizing DNTT of which benzene ring adjacent to the condensed heterocyclic ring in the central part is substituted.

The present invention also relates to a synthesis method, a use method and the like of the aromatic polymer of the present invention. Furthermore, the present invention relates to a solution, an organic semiconductor film, an organic semiconductor device and the like, each containing the aromatic polymer of the present invention.

Fourth and Fifth Aspects of the Present Invention

As a result of intensive studies, the present inventors have discovered a novel synthesis method of DNTT or a derivative thereof, an intermediate aromatic compound for the novel synthesis method, and a method for synthesizing the intermediate aromatic compound.

According to the present invention, DNTT or a derivative can be synthesized, without problems of the above-described conventional synthesis routes (1) and (2). Specifically, according to the present invention, 3-methylthio-2-naphthaldehyde (formula (b)) usable as an intermediate in the conventional synthesis route (1) is synthesized by a novel synthesis method, whereby DNTT or a derivative thereof can be synthesized, without problems of the above-described conventional synthesis routes (1) and (2).

MODE FOR CARRYING OUT THE INVENTION

Figure 1:
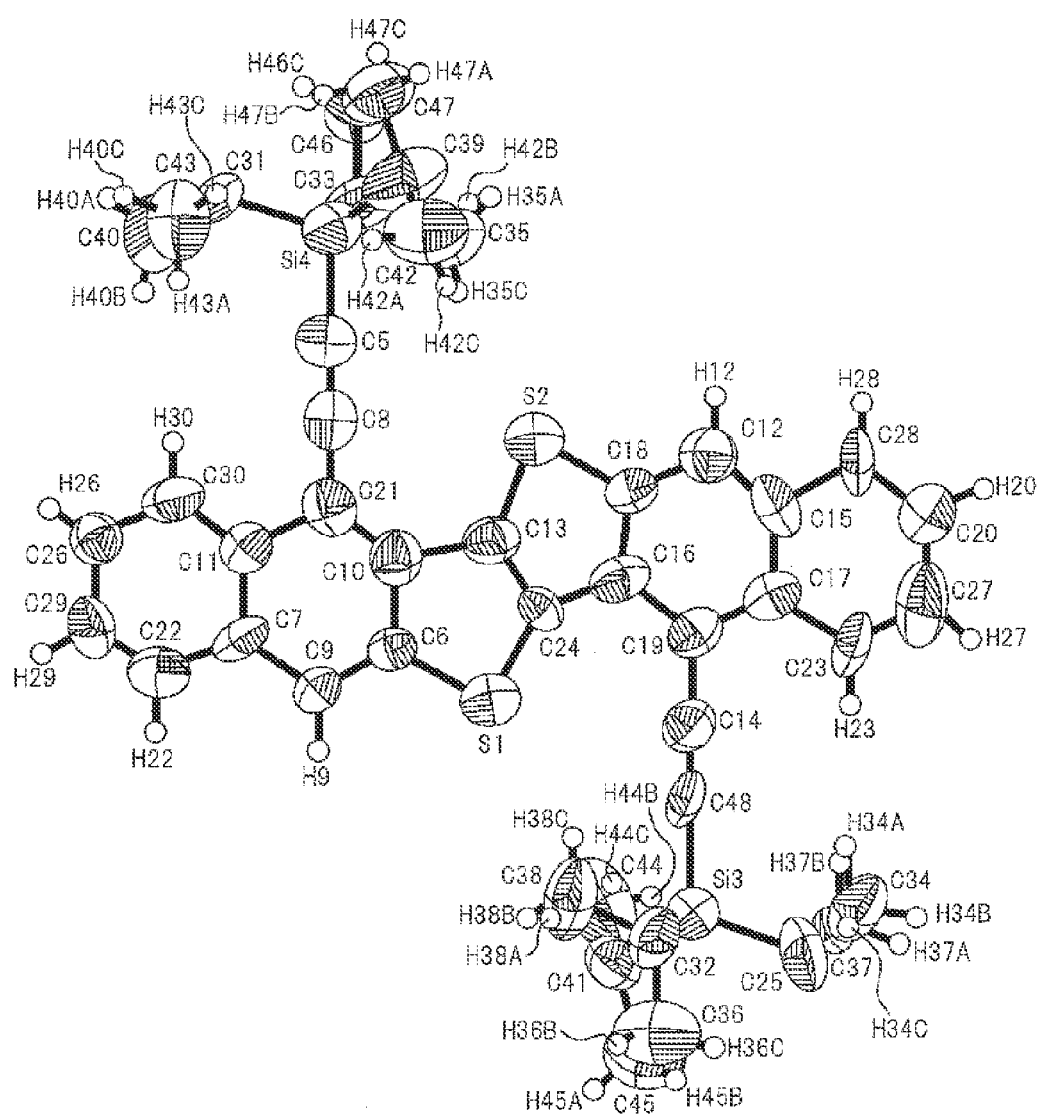
FIG. 1 A molecular structure ORTEP drawing based on the single-crystal structural analysis of di-TIPS-substituted DNTT obtained in Example A-2.

In the description of this specification, for the sake of brevity, the expression "an alkyl group having from 1 to 20 carbon atoms, an alkenyl group having from 2 to 20 carbon atoms, an alkynyl group having from 2 to 20 carbon atoms, a substituted or unsubstituted aromatic group having from 4 to 20 carbon atoms, a ketone group having from 2 to 10 carbon atoms, an amino group having from 1 to 20 carbon atoms, an amide group having from 1 to 20 carbon atoms, an imide group having from 1 to 20 carbon atoms, a sulfide group having from 1 to 20 carbon atoms, and an alkylsilylalkynyl group having from 1 to 40 carbon atoms" is referred to as "an alkyl group and the like".

The "aromatic group" in the "substituted or unsubstituted aromatic group having from 4 to 20 carbon atoms" may be a benzene-based aromatic group, a heterocyclic group or a non-benzene-based aromatic group. Specific benzene-based aromatic groups include a benzene group and a naphthalene group. Specific heterocyclic groups include a furan group, a thiophene group, a pyrrole group, and an imidazole group. Specific non-benzene-based aromatic groups include annulene and azulene. In the case where such an aromatic group is substituted, the substituent includes an alkyl group, an alkenyl group, an alkynyl group, an aromatic group, a ketone group, an amino group, an amide group, an imide group, and a sulfide group.

For example, when the "substituted or unsubstituted aromatic group having from 4 to 20 carbon atoms" is a substituted or unsubstituted thiophene group, the thiophene group may be further substituted with a substituted or unsubstituted thiophene group, as shown below.

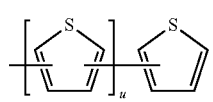

[Chem. 7]

(wherein u is an integer of 0 to 4).

Incidentally, when the aromatic group such as thiophene group is substituted, the substituent may be a halogen atom, an alkyl group, an alkenyl group, an alkynyl group, a substituted or unsubstituted aromatic group, a ketone group, an amino group, an amide group, an imide group, a sulfide group, an alkylsilylalkynyl group or the like.

Also, the "alkylsilylalkynyl group having from 1 to 40 carbon atoms" may be a trialkylsilylalkynyl group having from 1 to 40 carbon atoms, and particularly a trialkylsilylalkynyl group having the following formula:

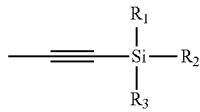

[Chem. 8]

(wherein each of $R_1$ to $R_3$ is independently an alkyl group having from 1 to 10 carbon atoms, and particularly a group selected from the group consisting of a methyl group, an ethyl group, an isopropyl group, an n-butyl group, a sec-butyl group and a tert-butyl group).

In the description of this specification, the "chalcogen" means oxygen, sulfur, selenium, tellurium or polonium, and particularly sulfur or selenium, and more particularly sulfur.

In the description of this specification, the "halogen" means fluorine, chlorine, bromine, iodine or astatine, particularly chlorine, bromine or iodine, and more particularly bromine.

In the description of this specification, the "substituted or unsubstituted aromatic group having from 4 to 20 carbon atoms" formed by combining two adjacent groups with each other may be, for example, a substituted or unsubstituted aromatic group having the following structure.

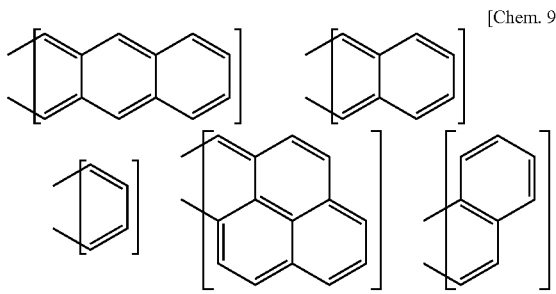

[Chem. 9]

In the description of this specification, with respect to "(D) a substituent having from 2 to 20 carbon atoms, which is obtained by adding a dienophilic alkene to a benzene ring", Patent Document 5 may be referred to for the dienophilic alkene. As to the method for adding such a dienophilic alkene to a benzene ring of a condensed polycyclic aromatic compound, Patent Document 5 may be referred to.

Incidentally, as described in Patent Document 5, the dienophilic alkene added to a benzene ring of a condensed polycyclic aromatic compound can decrease the crystallinity of the condensed polycyclic aromatic compound, and thereby can increase the solubility of the condensed polycyclic aromatic compound of the present invention having such a condensed polycyclic aromatic moiety. Also, in the case of producing a semiconductor film by using such a condensed polycyclic aromatic compound in a solution method, the coating film of a solution containing this compound is heated, whereby elimination and removal of the dienophilic alkene can be achieved together with removal of the solvent from the solution.

Specifically, the "(D) substituent having from 2 to 20 carbon atoms, which is obtained by adding a dienophilic alkene to a benzene ring" includes, for example, compounds of the following formulae (B-1a) and (B-2a), particularly the following formulae (B-1b) and (B-2b), and more particularly the following formulae (B-1c) and (B-2c).

[Chem. 10]

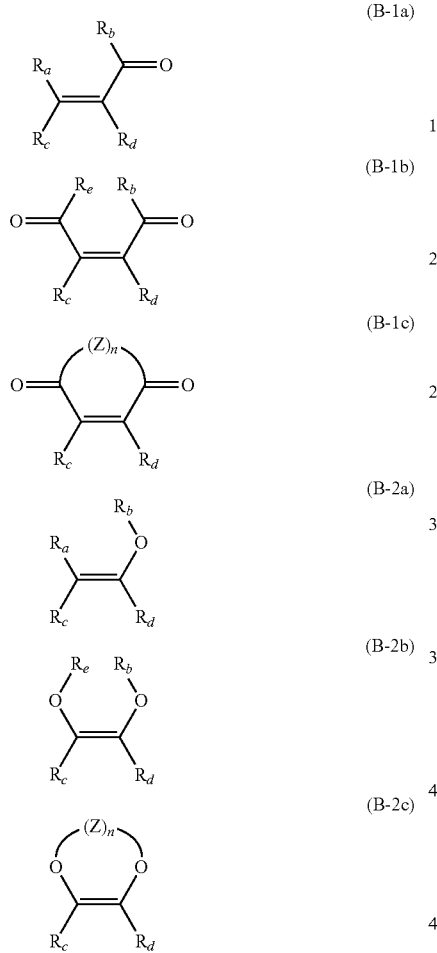

(wherein each of $R_a$, $R_b$, $R_c$ and $R_d$ is independently selected from the group consisting of a bond, hydrogen, a halogen, a hydroxyl group, an amide group, a mercapto group, a cyano group, an alkyl group having from 1 to 10 carbon atoms, an alkenyl group having from 2 to 10 carbon atoms, an alkynyl group having from 2 to 10 carbon atoms, an alkoxy group having from 1 to 10 carbon atoms, a substituted or unsubstituted aromatic group having from 4 to 10 carbon atoms, an ester group having from 1 to 10 carbon atoms, an ether group having from 1 to 10 carbon atoms, a ketone group having from 1 to 10 carbon atoms, an amino group having from 1 to 10 carbon atoms, an amide group having from 1 to 10 carbon atoms, an imide group having from 1 to 10 carbon atoms, and a sulfide group having from 1 to 10 carbon atoms;

$R_a$ and $R_b$ may combine with each other to form a ring,
$R_c$ and $R_d$ may combine with each other to form a ring,
n is an integer of 1 to 5, and
Z is selected from a group consisting of a bond (—), oxygen (—O—), a methylenic carbon (—C($R_r$)$_2$—), an ethylenic carbon (—C($R_r$)=), a carbonyl group (—C(=O)—), a nitrogen (—N($R_r$)—) and sulfur (—S—), and when n is 2 or more, each may be the same as or different from every other (each $R_r$ is independently selected from the group consisting of hydrogen, a halogen, an alkyl group having from 1 to 10 carbon atoms, an alkenyl group having from 2 to 10 carbon atoms, an alkynyl group having from 2 to 10 carbon atoms, an alkoxy group having from 1 to 10 carbon atoms, a substituted or unsubstituted aromatic group having from 4 to 10 carbon atoms, an ester group having from 1 to 10 carbon atoms, an ether group having from 1 to 10 carbon atoms, a ketone group having from 1 to 10 carbon atoms, an amino group having from 1 to 10 carbon atoms, an amide group having from 1 to 10 carbon atoms, an imide group having from 1 to 10 carbon atoms, and a sulfide group having from 1 to 10 carbon atoms).

More specifically, the dienophilic alkene includes compounds of the following formulae (B-1-1) to (B-2-3):

[Chem. 11]

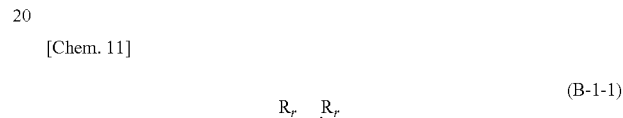

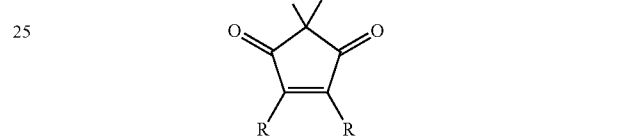

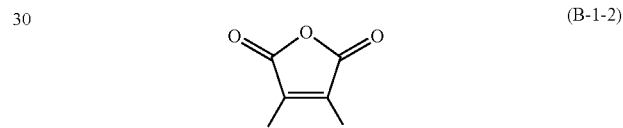

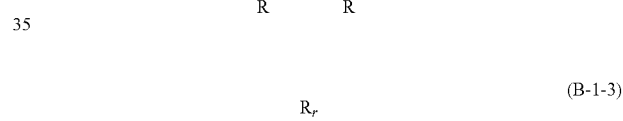

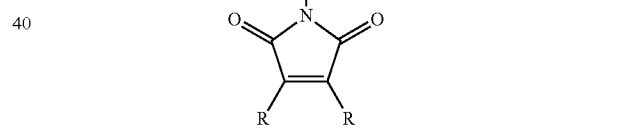

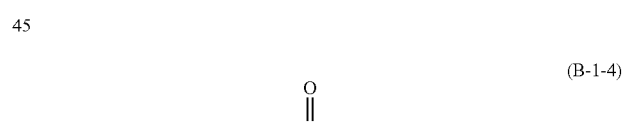

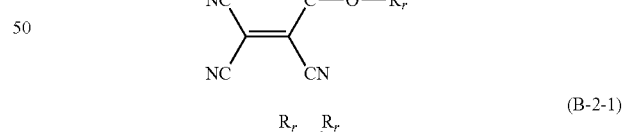

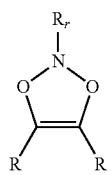

(B-2-3)

(wherein each of R and $R_r$ is independently selected from the group consisting of hydrogen, a halogen, a hydroxyl group, an amide group, a mercapto group, a cyano group, an alkyl group having from 1 to 10 carbon atoms, an alkenyl group having from 2 to 10 carbon atoms, an alkynyl group having from 2 to 10 carbon atoms, an alkoxy group having from 1 to 10 carbon atoms, a substituted or unsubstituted aromatic group having from 4 to 10 carbon atoms, an ester group having from 1 to 10 carbon atoms, an ether group having from 1 to 10 carbon atoms, a ketone group having from 1 to 10 carbon atoms, an amino group having from 1 to 10 carbon atoms, an amide group having from 1 to 10 carbon atoms, an imide group having from 1 to 10 carbon atoms, and a sulfide group having from 1 to 10 carbon atoms).

First Aspect of the Present Invention

Condensed Polycyclic Aromatic Compound

The condensed polycyclic aromatic compound of the first aspect of the present invention is represented by the following formula (I):

[Chem. 12]

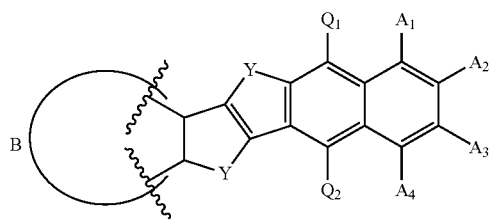

(I)

(wherein each of $Q_1$ and $Q_2$ is independently selected from the group consisting of a hydrogen atom, a halogen atom, an alkyl group and the like, and at least one of $Q_1$ and $Q_2$ is a group other than a hydrogen atom and a halogen atom;

B is a substituted or unsubstituted condensed ring having at least one benzene ring moiety;

each Y is independently selected from chalcogens; and each of $A_1$ to $A_4$ is independently selected from the group consisting of a hydrogen atom, a halogen atom, an alkyl group and the like, and two adjacent members out of $A_1$ to $A_4$ may combine with each other to form a substituted or unsubstituted aromatic group having from 4 to 20 carbon atoms).

The condensed polycyclic aromatic compound of the first aspect of the present invention is represented, for example, by the following formula (I-1):

[Chem. 13]

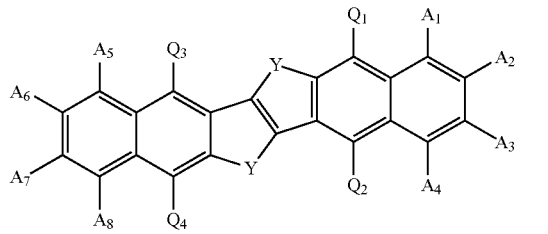

(I-1)

(wherein each of $Q_1$ to $Q_4$ is independently selected from the group consisting of a hydrogen atom, a halogen atom, an alkyl group and the like, and at least one of $Q_1$ to $Q_4$ is a group other than a hydrogen atom and a halogen atom;

each Y is independently selected from chalcogens; and each of $A_1$ to $A_8$ is independently selected from the group consisting of a hydrogen atom, a halogen atom, an alkyl group and the like, and two adjacent members out of $A_1$ to $A_8$ may combine with each other to form a substituted or unsubstituted aromatic group having from 4 to 20 carbon atoms).

In the compound of formula (I-1), for example, each of $Q_2$ and $Q_3$ is independently selected from the group consisting of a hydrogen atom, a halogen atom, an alkyl group and the like, at least one of $Q_2$ and $Q_3$ is a group other than a hydrogen atom and a halogen atom, and $Q_1$ and $Q_4$ are a hydrogen atom.

The compound of formula (I-1) may be particularly a compound represented by the following formula (I-1-1):

[Chem. 14]

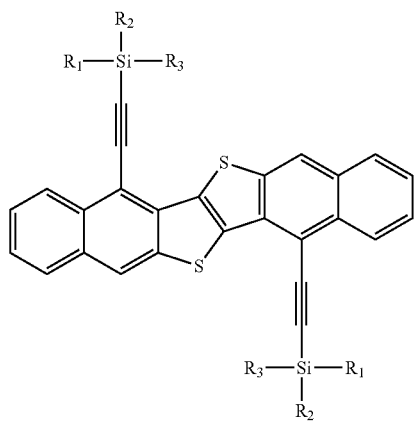

(I-1-1)

(wherein each of $R_1$ to $R_3$ is independently an alkyl group having from 1 to 10 carbon atoms).

The condensed polycyclic aromatic compound of the first aspect of the present invention is represented, for example, by the following formula (I-2):

[Chem. 15]

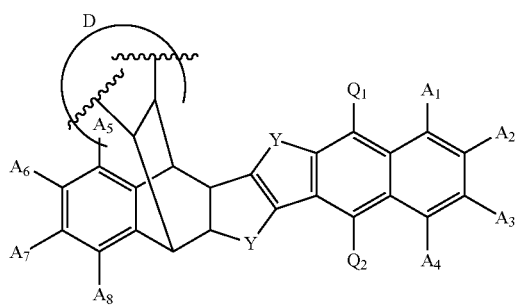

(I-2)

(wherein each of $Q_1$ and $Q_2$ is independently selected from the group consisting of a hydrogen atom, a halogen atom, an alkyl group and the like, and at least one of $Q_1$ and $Q_2$ is a group other than a hydrogen atom and a halogen atom;

D is a substituent having from 2 to 20 carbon atoms, which is obtained by adding a dienophilic alkene to a benzene ring;

each Y is independently selected from chalcogens; and each of $A_1$ to $A_8$ is independently selected from the group consisting of a hydrogen atom, a halogen atom, an alkyl group and the like, and two adjacent members out of $A_1$ to $A_8$ may combine with each other to form a substituted or unsubstituted aromatic group having from 4 to 20 carbon atoms).

In the compound of formula (I-2), for example, each of $Q_1$ and $Q_2$ is independently selected from the group consisting of an alkyl group and the like.

The compound of formula (I-2) may be particularly a compound represented by the following formula (I-2-1):

[Chem. 16]

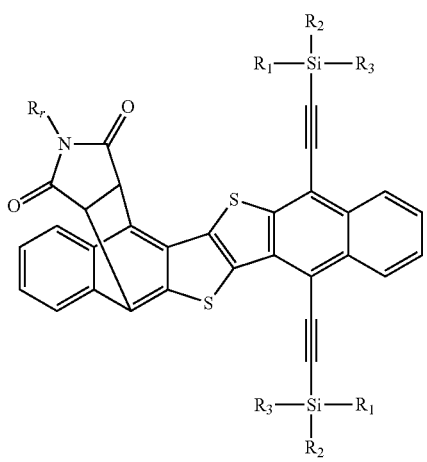

(I-2-1)

(wherein each of $R_1$ to $R_3$ is independently an alkyl group having from 1 to 10 carbon atoms, and $R_r$ is as described above).

In the compound of formula (I), and particularly in the compound of formula (I-1) or (I-2), $A_1$, $A_4$, $A_5$ and $A_8$, and particularly $A_1$ to $A_8$, may be a hydrogen atom. Also, in the compound of formula (I), and particularly of formula (I-1) or (I-2), Y may be a sulfur atom.

First Aspect of the Present Invention

Condensed Polycyclic Aromatic Compound-Containing Solution

The condensed polycyclic aromatic compound-containing solution of the first aspect of the present invention contains an organic solvent, and the condensed polycyclic aromatic compound of the first aspect of the present invention which is at least partially dissolved in the organic solvent.

The condensed polycyclic aromatic compound-containing solution may contain the condensed polycyclic aromatic compound of the first aspect of the present invention at any concentration. For example, the solution may contain the condensed polycyclic aromatic compound of the first aspect of the present invention at a concentration of 0.01 to 10 mass %, from 0.05 to 5 mass %, or from 0.1 to 3 mass %.

The organic solvent which can be used here includes any organic solvent capable of dissolving the condensed polycyclic aromatic compound of the first aspect of the present invention without deteriorating the compound. Specifically, for example, an aprotic polar solvent such as N-methylpyrrolidone, dimethylsulfoxide, acetonitrile and ethyl acetate; an ether-based solvent such as diethyl ether, tetrahydrofuran, diisopropyl ether, diethylene glycol dimethyl ether and 1,4-dioxane; aromatic hydrocarbons such as benzene, toluene, xylene and mesitylene (i.e., 1,3,5-trimethylbenzene); aliphatic hydrocarbons such as hexane and heptane; and a halogen-containing solvent such as dichloromethane, chloroform and dichloroethane may be considered as the organic solvent.

First Aspect of the Present Invention

Production Method of Organic Semiconductor Film

The method of the first aspect of the present invention for producing an organic semiconductor film comprises coating a substrate with the condensed polycyclic aromatic compound-containing solution of the first aspect of the present invention, and removing the organic solvent from the solution coated on the substrate.

Coating of the solution on a substrate may be performed in any manner and, for example, may be performed by a casting method, a spin coating method or a printing method. Also, coating of the solution on a substrate may be performed by merely dropping the solution on the substrate.

Removal of the organic solvent from the solution may be performed simultaneously with the coating step.

Removal of the organic solvent from the solution may also be accelerated by heating. In this case, the heating can be performed at any temperature involving substantially no decomposition of the condensed polycyclic aromatic compound of the first aspect of the present invention, for example, at a temperature of 80° C. or more, 100° C. or more, 120° C. or more, or 140° C. or more, and 200° C. or less, 220° C. or less, 240° C. or less, or 260° C. or less. Such heating can be achieved, for example, by bringing the solution-coated substrate into direct contact with a heated thing such as heated electric heater, introducing the substrate into a heated region such as heated furnace, or irradiating the substrate with an electromagnetic wave such as infrared ray and microwave.

Incidentally, in the case of the compound of the first aspect of the present invention, which is intended to constitute an organic semiconductor film by eliminating an addition compound, for example, in the case of the compound of formula (I-2), elimination and removal of the substituent represented by D can be achieved together with removal of the organic solvent. This elimination reaction can be accelerated by heating.

First Aspect of the Present Invention

Manufacturing Method of Organic Semiconductor Device

The method of the first aspect of the present invention for manufacturing an organic semiconductor device comprises producing an organic semiconductor film by the method of the first aspect of the present invention for producing an organic semiconductor film.

Also, this method may optionally further comprise forming an electrode layer and/or a dielectric layer on the top side or bottom side of the organic semiconductor film.

First Aspect of the Present Invention

Organic Semiconductor Device

The organic semiconductor device of the first aspect of the present invention has an organic semiconductor film containing the condensed polycyclic aromatic compound of the first aspect of the present invention.

The context in which the organic semiconductor film contains the compound of the first aspect of the present invention means that the organic semiconductor film contains the compound of the first aspect of the present invention at least in a detectable amount.

Accordingly, for example, in the case of the compound of the first aspect of the present invention, which is intended to constitute directly the organic semiconductor film, for example, in the case of the compound of formula (I-1), the compound constitutes the substantial portion of the organic semiconductor, i.e. the organic semiconductor film is substantially composed of the compound of the first aspect of the present invention.

Also, in the case of the compound of the first aspect of the present invention, which is intended to constitute the organic semiconductor film by eliminating an addition compound, for example, in the case of the compound of formula (I-2), a compound having still attached thereto an addition compound is sometimes contained as a trace component of the organic semiconductor. In this case, the molar ratio of the compound having still attached thereto an addition compound may be more than 1 ppm, more than 10 ppm, more than 100 ppm, more than 1,000 ppm, or more than 10,000 ppm (1%). Also, the ratio of the compound having still attached thereto an addition compound may be 10 mol % or less, 5 mol % or less, 3 mol % or less, 1 mol % or less, 0.1 mol % or less, or 0.01 mol % or less.

In particular, the organic semiconductor device of the present invention is a thin-film transistor having a source electrode, a drain electrode, a gate electrode, a gate insulating film and the organic semiconductor film, and this is a thin-film transistor in which the source electrode and the drain electrode are insulated from the gate electrode by the gate insulating film and the current flowing through the organic semiconductor from the source electrode to the drain electrode is controlled by the voltage applied to the gate electrode. Also, in particular, the organic semiconductor device of the present invention is a solar cell having the organic semiconductor film as an active layer. Incidentally, the "organic semiconductor device" as used in the present invention means a device having an organic semiconductor film, and other layers such as electrode layer and dielectric layer may be formed of an inorganic material or an organic material.

Second Aspect of the Present Invention

Condensed Polycyclic Aromatic Compound

The condensed polycyclic aromatic compound of the second aspect of the present invention is represented by the following formula (II):

[Chem. 17]

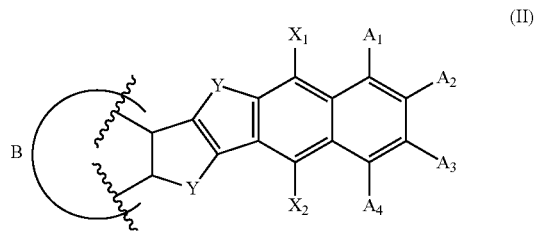

(wherein each of $X_1$ and $X_2$ is independently selected from the group consisting of a hydrogen atom, a halogen atom, an alkyl group and the like, and at least one of $X_1$ and $X_2$ is a halogen atom;

B is a condensed ring having at least one benzene ring moiety;

each Y is independently selected from chalcogens; and each of $A_1$ to $A_4$ is independently selected from the group consisting of a hydrogen atom, a halogen atom, an alkyl group and the like, and two adjacent members out of $A_1$ to $A_4$ may combine with each other to form a substituted or unsubstituted aromatic group having from 4 to 20 carbon atoms).

The condensed polycyclic aromatic compound of the second aspect of the present invention is represented, for example, by the following formula (II-1):

[Chem. 18]

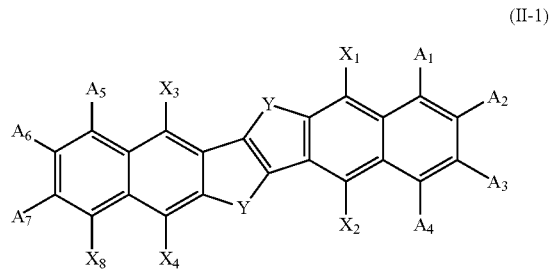

(wherein each of $X_1$ to $X_4$ is independently selected from the group consisting of a hydrogen atom, a halogen atom, an alkyl group and the like, and at least one of $X_1$ to $X_4$ is a halogen atom;

each Y is independently selected from chalcogens; and each of $A_1$ to $A_8$ is independently selected from the group consisting of a hydrogen atom, a halogen atom, an alkyl group and the like, and two adjacent members out of $A_1$ to $A_8$ may combine with each other to form a substituted or unsubstituted aromatic group having from 4 to 20 carbon atoms).

In the compound of formula (II-1), for example, each of $X_2$ and $X_3$ is independently selected from the group consisting of a hydrogen atom, a halogen atom, an alkyl group and the like, at least one of $X_2$ and $X_3$ is a halogen atom, and $X_1$ and $X_4$ are a hydrogen atom.

The compound of formula (II-1) may be particularly a compound represented by the following formula (II-1-1):

[Chem. 19]

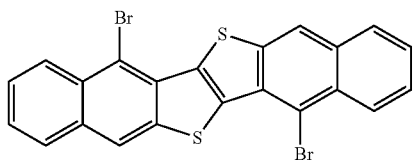

(II-1-1)

The compound of formula (II-1) may be particularly a compound represented by the following formula (II-1-2):

[Chem. 20]

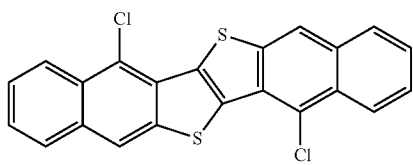

(II-1-2)

The condensed polycyclic aromatic compound of the second aspect of the present invention is represented, for example, by the following formula (II-2):

[Chem. 21]

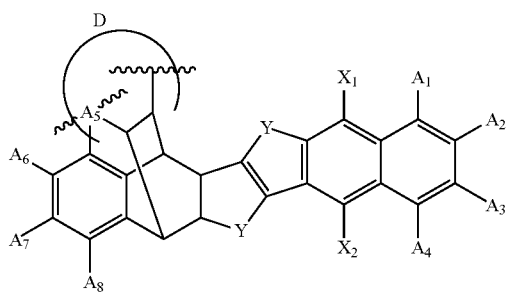

(II-2)

(wherein each of $X_1$ and $X_2$ is independently selected from the group consisting of a hydrogen atom, a halogen atom, an alkyl group and the like, and at least one of $X_1$ and $X_2$ is a halogen atom;

D is a substituent having from 2 to 20 carbon atoms, which is obtained by adding a dienophilic alkene to a benzene ring;

each Y is independently selected from chalcogens; and each of $A_1$ to $A_8$ is independently selected from the group consisting of a hydrogen atom, a halogen atom, an alkyl group and the like, and two adjacent members out of $A_1$ to $A_8$ may combine with each other to form a substituted or unsubstituted aromatic group having from 4 to 20 carbon atoms).

In the compound of formula (II-2), for example, both $X_1$ and $X_2$ are a halogen atom.

The compound of formula (II-2-1) may be particularly a compound represented by the following formula (I-2-1):

[Chem. 22]

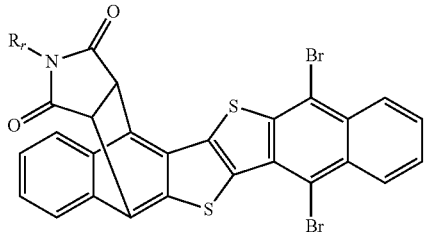

(II-2-1)

(wherein $R_r$ is as described above).

In the compound of formula (I), and particularly in the compound of formula (I-1) or (1-2), $A_1$, $A_4$, $A_5$ and $A_8$, and particularly $A_1$ to $A_8$, may be a hydrogen atom. Also, in the compound of formula (I), and particularly in the compound of formula (I-1) or (I-2), Y may be a sulfur atom.

Second Aspect of the Present Invention

Synthesis Method of Condensed Polycyclic Aromatic Compound of Second Aspect of the Present Invention The method for synthesizing the condensed polycyclic aromatic compound of the second aspect of the present invention includes the following steps:

(a) providing a composition containing an organic solvent and a condensed polycyclic aromatic compound represented by the following formula (III):

[Chem. 23]

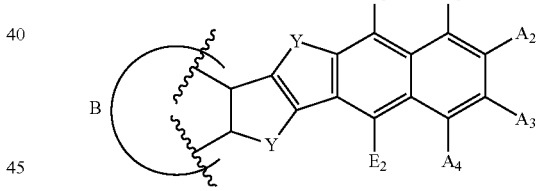

(III)

(wherein each of $E_1$ and $E_2$ is independently selected from the group consisting of a hydrogen atom, a halogen atom, an alkyl group and the like, and at least one of $E_1$ and $E_2$ is a hydrogen atom;

B is a condensed ring having at least one benzene ring moiety;

each Y is independently selected from chalcogens; and each of $A_1$ to $A_4$ is independently selected from the group consisting of a hydrogen atom, a halogen atom, an alkyl group and the like, and two adjacent members out of $A_1$ to $A_4$ may combine with each other to form a substituted or unsubstituted aromatic group having from 4 to 20 carbon atoms), and (b) adding a halogen to the composition.

The organic solvent which can be used here includes any organic solvent capable of dissolving and/or dispersing the condensed polycyclic aromatic compound represented by the following formula (III). Specifically, for example, an aprotic polar solvent such as N-methylpyrrolidone, dimethylsulfoxide, acetonitrile and ethyl acetate; an ether-based solvent such as diethyl ether, tetrahydrofuran, diisopropyl ether, diethylene glycol dimethyl ether and 1,4-dioxane; aromatic hydrocarbons such as benzene, toluene, xylene and mesitylene (i.e., 1,3,5-trimethylbenzene); aliphatic hydrocarbons such as hexane and heptane; and a halogen-containing solvent such as dichloromethane, chloroform and dichloroethane may be considered as the organic solvent.

Addition of a halogen to the composition containing the condensed polycyclic aromatic compound represented by formula (III) can be performed by any method. For example, fluorine or chlorine can be added by bubbling, and bromine, iodine or astatine can be added as a liquid or a solid. Also, in order to accelerate the reaction of the compound represented by formula (III) and a halogen, heating may be performed.

The compound of formula (III) is represented, for example, by the following formula (III-1):

[Chem. 24]

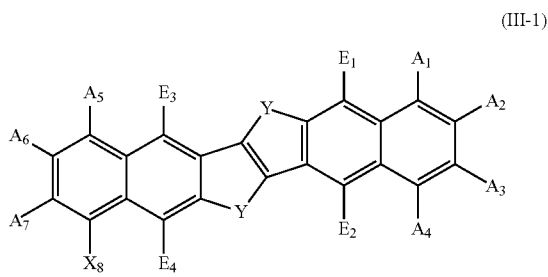

(III-1)

(wherein each of $E_1$ to $E_4$ is independently selected from the group consisting of a hydrogen atom, a halogen atom, an alkyl group and the like, and at least one of $E_1$ to $E_4$ is a hydrogen atom;

each Y is independently selected from chalcogens; and each of $A_1$ to $A_8$ is independently selected from the group consisting of a hydrogen atom, a halogen atom, an alkyl group and the like, and two adjacent members out of $A_1$ to $A_8$ may combine with each other to form a substituted or unsubstituted aromatic group having from 4 to 20 carbon atoms).

In the compound of formula (III-1), for example, all of $E_1$ to $E_4$ are a hydrogen atom.

The compound of formula (III) is represented, for example, by the following formula (III-2):

[Chem. 25]

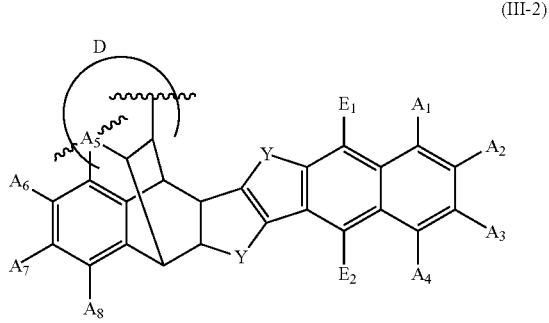

(III-2)

(wherein each of $E_1$ and $E_2$ is independently selected from the group consisting of a hydrogen atom, a halogen atom, an alkyl group and the like, and at least one of $E_1$ and $E_2$ is a hydrogen atom;

D is a substituent having from 2 to 20 carbon atoms, which is obtained by adding a dienophilic alkene to a benzene ring;

each Y is independently selected from chalcogens; and each of $A_1$ to $A_8$ is independently selected from the group consisting of a hydrogen atom, a halogen atom, an alkyl group and the like, and two adjacent members out of $A_1$ to $A_8$ may combine with each other to form a substituted or unsubstituted aromatic group having from 4 to 20 carbon atoms).

In the compound of formula (III-2), for example, both $E_1$ and $E_2$ are hydrogen.

The compound of formula (III-2) may be particularly a compound represented by the following formula (III-2-1):

[Chem. 26]

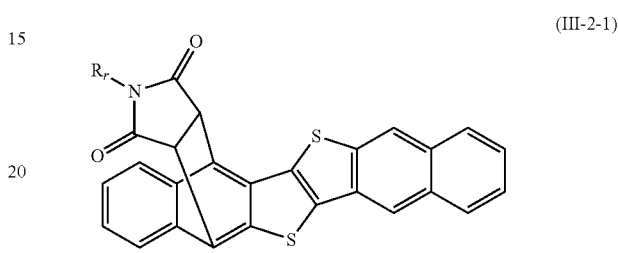

(III-2-1)

(wherein $R_r$ is as described above).

Second Aspect of the Present Invention

Use Method of Compound of Second Aspect of the Present Invention (Synthesis Method of Condensed Polycyclic Aromatic Compound of First Aspect of the Present Invention)

The use method of the second aspect of the present invention, i.e. the method for synthesizing the condensed polycyclic aromatic compound of the first aspect of the present invention from the second aspect of the present invention, includes the following steps:

(a) providing a composition containing an organic solvent and a condensed polycyclic aromatic compound of the second aspect of the present invention, and (b) substituting at least one halogen atom out of $X_1$ to $X_4$ with a substituent selected from the group consisting of an alkyl group and the like.

The organic solvent which can be used here includes any organic solvent capable of dissolving and/or dispersing the compound of the second aspect of the present invention, i.e. the compound of formula (II). Specifically, for example, an aprotic polar solvent such as N-methylpyrrolidone, dimethylsulfoxide, acetonitrile and ethyl acetate; an ether-based solvent such as diethyl ether, tetrahydrofuran, diisopropyl ether, diethylene glycol dimethyl ether and 1,4-dioxane; aromatic hydrocarbons such as benzene, toluene, xylene and mesitylene (i.e., 1,3,5-trimethylbenzene); aliphatic hydrocarbons such as hexane and heptane; and a halogen-containing solvent such as dichloromethane, chloroform and dichloroethane may be considered as the organic solvent.

The reaction of substituting at least one halogen atom out of $X_1$ to $X_4$ in the compound represented by formula (II) with a substituent selected from the group consisting of an alkyl group and the like can be performed by various coupling method using an aromatic halide, i.e. Mizoroki-Heck reaction, Negishi coupling, Migita-Kosugi-Stille coupling, Sonogashira coupling, Suzuki-Miyaura coupling, Buchwald-Hartwig reaction or Kumada-Tamao-Corriu coupling. In order to accelerate this coupling reaction, heating may be performed.

Incidentally, the outline of each coupling reaction is as follows (Ar is an aromatic moiety, X is a halogen, and R is hydrogen, an alkyl group or the like).

(1) Mizoroki-Heck Reaction

Ar—X+H$_2$C=CHR (+Pd catalyst)÷Ar—HC=CHR (2) Negishi Coupling

Ar—X+R—Zn—X (+Pd catalyst)÷Ar—R (3) Migita-Kosugi-Stille Coupling

Ar—X+R—Sn—R'$_3$ (+Pd catalyst)÷Ar—R (4) Sonogashira Coupling

Ar—X+R—C≡C—H (+Pd catalyst)+base÷Ar—C≡C—R (5) Suzuki-Miyaura Coupling

Ar—X+R—B (OH)$_2$ (+Pd catalyst)+base÷Ar—R (6) Buchwald-Hartwig Reaction

Ar—X+R—NH$_2$ (+Pd catalyst)+base÷Ar—NHR (7) Kumada-Tamao-Corriu Coupling

Ar—X+R—Mg—X (+Ni catalyst)÷Ar—R

Third Aspect of the Present Invention

Aromatic Polymer

The aromatic polymer of the third aspect of the present invention contains two or more condensed polycyclic aromatic moieties represented by the following formula (IV):

[Chem. 27]

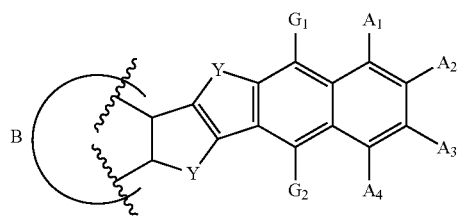

(IV)

(wherein each of G$_1$ and G$_2$ is independently selected from the group consisting of a bond, a hydrogen atom, a halogen atom, an alkyl group and the like, and at least one of G$_1$ and G$_2$ is a bond;

B is a condensed ring having at least one benzene ring moiety;

each Y is independently selected from chalcogens; and each of A$_1$ to A$_4$ is independently selected from the group consisting of a hydrogen atom, a halogen atom, an alkyl group and the like, and two adjacent members out of A$_1$ to A$_4$ may combine with each other to form a substituted or unsubstituted aromatic group having from 4 to 20 carbon atoms).

The condensed polycyclic aromatic moiety is represented, for example, by the following formula (IV-1):

[Chem. 28]

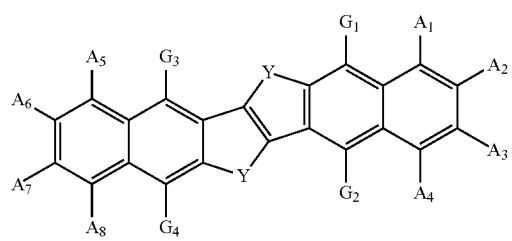

(IV-1)

(wherein each of G$_1$ to G$_4$ is independently selected from the group consisting of a bond, a hydrogen atom, a halogen atom, an alkyl group and the like, and at least one of G$_1$ to G$_4$ is a bond;

each Y is independently selected from chalcogens; and each of A$_1$ to A$_8$ is independently selected from the group consisting of a hydrogen atom, a halogen atom, an alkyl group and the like, and two adjacent members out of A$_1$ to A$_8$ may combine with each other to form a substituted or unsubstituted aromatic group having from 4 to 20 carbon atoms).

In the condensed polycyclic aromatic moiety of formula (IV-1), for example, G$_2$ and G$_3$ are a bond, and G$_1$ and G$_4$ are a hydrogen atom.

The condensed polycyclic aromatic moiety of formula (IV-1) may be particularly a moiety represented by the following formula (IV-1-1):

[Chem. 29]

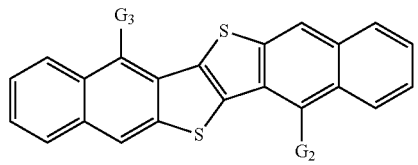

(IV-1-1)

The condensed polycyclic aromatic moiety is represented, for example, by the following formula (IV-2):

[Chem. 30]

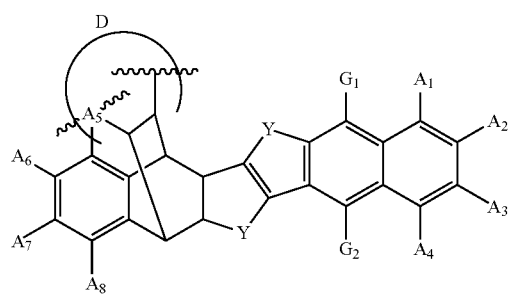

(IV-2)

(wherein each of G$_1$ and G$_2$ is independently selected from the group consisting of a bond, a hydrogen atom, a halogen atom, an alkyl group and the like, and at least one of G$_1$ and G$_2$ is a bond;

D is a substituent having from 2 to 20 carbon atoms, which is obtained by adding a dienophilic alkene to a benzene ring;

each Y is independently selected from chalcogens; and each of $A_1$ to $A_8$ is independently selected from the group consisting of a hydrogen atom, a halogen atom, an alkyl group and the like, and two adjacent members out of $A_1$ to $A_8$ may combine with each other to form a substituted or unsubstituted aromatic group having from 4 to 20 carbon atoms).

In the condensed polycyclic aromatic moiety of formula (IV-2), for example, both $G_1$ and $G_2$ are a bond.

The condensed polycyclic aromatic moiety of formula (IV-2) may be particularly a compound represented by the following formula (IV-2-1):

[Chem. 31]

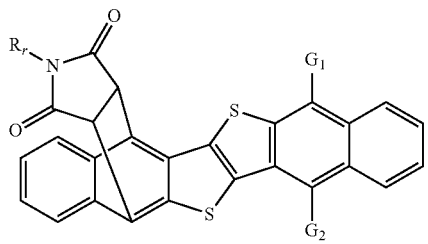

(IV-2-1)

(wherein each of $G_2$ and $G_3$ is a bond, and $R_r$ is as described above).

The aromatic polymer of the third aspect of the present invention contains, for example, a repeating unit of the following formula (V):

(V)

(wherein $T_T$ is the condensed polycyclic aromatic moiety above; and $Q_Q$ is a bond or a divalent group).

Also, the aromatic polymer of the third aspect of the present invention contains, for example, a repeating unit of the following formula (V-1):

[Chem. 32]

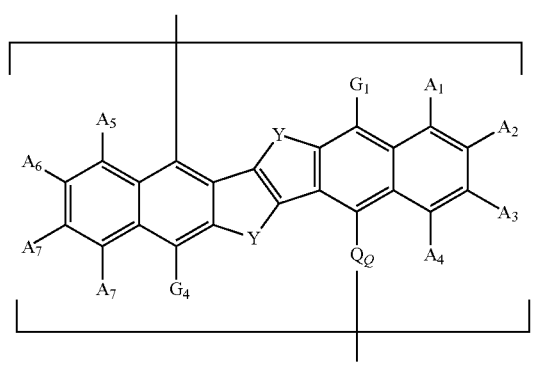

(V-1)

(wherein each of $G_1$ and $G_4$ is independently selected from the group consisting of a bond, a hydrogen atom, a halogen atom, an alkyl group and the like;

each Y is independently selected from chalcogens;

each of $A_1$ to $A_8$ is independently selected from the group consisting of a hydrogen atom, a halogen atom, an alkyl group and the like, and two adjacent members out of $A_1$ to $A_8$ may combine with each other to form a substituted or unsubstituted aromatic group having from 4 to 20 carbon atoms; and $Q_Q$ is a bond or a divalent group).

Incidentally, the bond as $Q_Q$ is not particularly limited as long as it is bondable to an adjacent unit, and the bond may be, for example, any of a single bond, a double bond and a triple bond.

Also, the divalent group as $Q_Q$ is not particularly limited as long as it is bondable to an adjacent unit, and the divalent group is, for example, a hydrocarbon group having from 1 to 40 carbon atoms, which may be accompanied by a heteroatom such as oxygen and nitrogen, and may be selected from the group consisting of an alkylene group having from 1 to 20 carbon atoms, an alkenylene group having from 2 to 20 carbon atoms, an alkynylene group having from 2 to 20 carbon atoms, a substituted or unsubstituted divalent aromatic group having from 4 to 20 carbon atoms, a divalent ketone group having from 2 to 10 carbon atoms, a divalent amino group having from 1 to 20 carbon atoms, a divalent amide group having from 1 to 20 carbon atoms, a divalent imide group having from 1 to 20 carbon atoms, a divalent sulfide group having from 1 to 20 carbon atoms, and a divalent alkylsilylalkynyl group having from 1 to 40 carbon atoms.

The "aromatic group" in the "substituted or unsubstituted divalent aromatic group having from 4 to 20 carbon atoms" may be a benzene-based aromatic group, a heterocyclic group or a non-benzene-based aromatic group. Specific benzene-based aromatic groups include a benzene group and a naphthalene group. Specific heterocyclic groups include a furan group, a thiophene group, a pyrrole group, and an imidazole group. Specific non-benzene-based aromatic groups include annulene and azulene. In the case where such an aromatic group is substituted, the substituent includes an alkyl group, an alkenyl group, an alkynyl group, an aromatic group, a ketone group, an amino group, an amide group, an imide group, and a sulfide group.

For example, when the "substituted or unsubstituted divalent aromatic group having from 4 to 20 carbon atoms" is a substituted or unsubstituted thiophene group, the thiophene group may be further substituted with a substituted or unsubstituted thiophene group as shown below.

[Chem. 33]

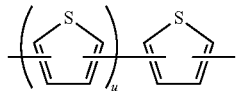

(wherein u is an integer of 0 to 4).

Incidentally, when the aromatic group such as thiophene group is substituted, the substituent may be a halogen atom, an alkyl group, an alkenyl group, an alkynyl group, a substituted or unsubstituted aromatic group, a ketone group, an amino group, an amide group, an imide group, a sulfide group, an alkylsilylalkynyl group or the like.

In the aromatic polymer of the third aspect of the present invention, the molecular weight obtained in terms of polystyrene by gel permeation chromatography (GPC) may be 1,000 or more, 2,000 or more, 3,000 or more, 4,000 or more, or 5,000 or more. Also, in aromatic polymer of the third aspect of the present invention, the molecular weight obtained in terms of polystyrene by GPC may be 500,000 or less, 100,000 or less, 100,000 or less, 50,000 or less, or 30,000 or less.

Third Aspect of the Present Invention

Synthesis Method

The method for synthesizing the aromatic polymer of the third aspect of the present invention includes the following steps:

(a) providing a composition containing an organic solvent and a condensed polycyclic aromatic compound represented by the following formula (II):

[Chem. 34]

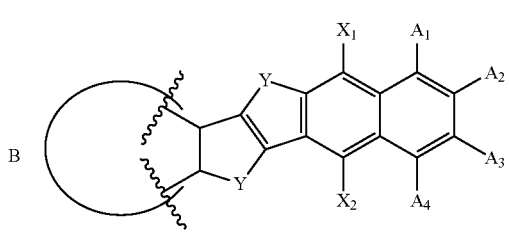

(II)

(wherein each of $X_1$ and $X_2$ is independently selected from the group consisting of a hydrogen atom, a halogen atom, an alkyl group and the like, and at least one of $X_1$ and $X_2$ is a halogen atom;

B is a condensed ring having at least one benzene ring moiety;

each Y is independently selected from chalcogens; and each of $A_1$ to $A_4$ is independently selected from the group consisting of a hydrogen atom, a halogen atom, an alkyl group and the like, and two adjacent members out of $A_1$ to $A_4$ may combine with each other to form a substituted or unsubstituted aromatic group having from 4 to 20 carbon atoms); and (b) adding, to the composition, a bonding compound having two or more moieties capable of substituting at least one halogen atom out of $X_1$ and $X_2$ to combine two or more condensed polycyclic aromatic compounds with each other.

As the moiety capable of substituting a halogen atom of the bonding compound used in the step (b), i.e. a moiety capable of substituting a halogen of an aromatic halide, various moieties are known. As the reaction using such a moiety, a coupling reaction such as Mizoroki-Heck reaction, Negishi coupling, Migita-Kosugi-Stille coupling, Sonogashira coupling, Suzuki-Miyaura coupling, Buchwald-Hartwig reaction, and Kumada-Tamao-Corriu coupling is known.

The organic solvent which can be used here includes any organic solvent capable of dissolving and/or dispersing the condensed polycyclic aromatic compound represented by the following formula (II). Specifically, for example, an aprotic polar solvent such as N-methylpyrrolidone, dimethylsulfoxide, acetonitrile and ethyl acetate; an ether-based solvent such as diethyl ether, tetrahydrofuran, diisopropyl ether, diethylene glycol dimethyl ether and 1,4-dioxane; aromatic hydrocarbons such as benzene, toluene, xylene and mesitylene (i.e., 1,3,5-trimethylbenzene); aliphatic hydrocarbons such as hexane and heptane; and a halogen-containing solvent such as dichloromethane, chloroform and dichloroethane may be considered as the organic solvent.

Addition of a bonding compound to the composition containing the condensed polycyclic aromatic compound represented by formula (II) can be performed by any method. For example, the bonding compound may be added as it is, or the bonding compound may be previously diluted with an organic solvent and then added. Also, in order to accelerate the reaction of the compound represented by formula (II) and the bonding compound, heating may be performed.

Incidentally, with respect to the compound of formula (II) used in the method for synthesizing the aromatic polymer of the third aspect of the present invention, the description related to the second aspect of the present invention can be referred to.

Third Aspect of the Present Invention

Aromatic Polymer-Containing Solution

The aromatic polymer-containing solution of the third aspect of the present invention contains an organic solvent and the aromatic polymer of the third aspect of the present invention which is at least partially dissolved in the organic solvent.

The aromatic polymer-containing solution can contain the aromatic polymer of the third aspect of the present invention at any concentration and, for example, may contain the aromatic polymer of the third aspect of the present invention at a concentration of 0.01 to 10 mass %, from 0.05 to 5 mass %, or from 0.1 to 3 mass %.

The organic solvent which can be used here includes any organic solvent capable of dissolving the aromatic polymer of the third aspect of the present invention without deteriorating the polymer. Specifically, for example, an aprotic polar solvent such as N-methylpyrrolidone, dimethylsulfoxide, acetonitrile and ethyl acetate; an ether-based solvent such as diethyl ether, tetrahydrofuran, diisopropyl ether, diethylene glycol dimethyl ether and 1,4-dioxane; aromatic hydrocarbons such as benzene, toluene, xylene and mesitylene (i.e., 1,3,5-trimethylbenzene); aliphatic hydrocarbons such as hexane and heptane; and a halogen-containing solvent such as dichloromethane, chloroform and dichloroethane may be considered as the organic solvent.

Third Aspect of the Present Invention

Production Method of Organic Semiconductor Film

The method of the third aspect of the present invention for producing an organic semiconductor film comprises coating a substrate with the aromatic polymer-containing solution of the third aspect of the present invention, and removing the organic solvent from the solution coated on the substrate.

Coating of the solution on a substrate may be performed in any manner and, for example, may be performed by a casting method, a spin coating method or a printing method. Also, coating of the solution on a substrate may be performed by merely dropping the solution on the substrate.

Removal of the organic solvent from the solution may be performed simultaneously with the coating step.

Removal of the organic solvent from the solution may also be accelerated by heating. In this case, the heating can be performed at any temperature involving substantially no decomposition of the aromatic polymer of the third aspect of the present invention, for example, at a temperature of 80° C. or more, 100° C. or more, 120° C. or more, or 140° C. or more, and 200° C. or less, 220° C. or less, 240° C. or less, or 260° C. or less. Such heating can be achieved, for example, by bringing the solution-coated substrate into direct contact with a heated thing such as heated electric heater, introducing the substrate into a heated region such as heated furnace, or irradiating the substrate with an electromagnetic wave such as infrared ray and microwave.

Incidentally, in the case of the aromatic polymer of the third aspect of the present invention, which is intended to constitute an organic semiconductor film by eliminating an addition compound, for example, in the case of the aromatic polymer of formula (IV-2), elimination and removal of the substituent represented by D can be achieved together with removal of the organic solvent. This elimination reaction can be accelerated by heating.

(Manufacturing Method of Organic Semiconductor Device)

The method of the third aspect of the present invention for manufacturing an organic semiconductor device comprises producing an organic semiconductor film by the method of the third aspect of the present invention for producing an organic semiconductor film.

Also, this method may optionally further comprise forming an electrode layer and/or a dielectric layer on the top side or bottom side of the organic semiconductor film.

Third Aspect of the Present Invention

Organic Semiconductor Device

The organic semiconductor device of the third aspect of the present invention has an organic semiconductor film containing the aromatic polymer of the third aspect of the present invention.

The context in which the organic semiconductor film contains the aromatic polymer of the third aspect of the present invention means that the organic semiconductor film contains the aromatic polymer of the third aspect of the present invention at least in a detectable amount.

Accordingly, for example, in the case of the aromatic polymer of the third aspect of the present invention, which is intended to constitute directly the organic semiconductor film, for example, in the case of the aromatic polymer of formula (IV-1), the aromatic polymer constitutes the substantial portion of the organic semiconductor, i.e. the organic semiconductor film is substantially composed of the aromatic polymer of the third aspect of the present invention.

In particular, the organic semiconductor device of the third aspect of the present invention is a thin-film transistor having a source electrode, a drain electrode, a gate electrode, a gate insulating film and the organic semiconductor film, and this is a thin-film transistor in which the source electrode and the drain electrode are insulated from the gate electrode by the gate insulating film and the current flowing through the organic semiconductor from the source electrode to the drain electrode is controlled by the voltage applied to the gate electrode. Also, in particular, the organic semiconductor device of the third aspect of the present invention is a solar cell having the organic semiconductor film as an active layer. Incidentally, the "organic semiconductor device" as used in the present invention means a device having an organic semiconductor film, and other layers such as electrode layer and dielectric layer may be formed of an inorganic material or an organic material.

Fourth Aspect of the Present Invention

Synthesis Method 1 of Intermediate

The method of the fourth aspect of the present invention for synthesizing a compound of the following formula (b), i.e. the method of the fourth aspect of the present invention for synthesizing a compound of the following formula (b) usable as an intermediate for the synthesis of DNTT or a derivative thereof, comprises reducing the cyano group of a compound of the following formula (i):

[Chem. 35]

formula (i)

[Chemical structure: naphthalene ring with substituents $A_4$, $X_2$, $A_3$, CN, $A_2$, SMe, $A_1$, $X_1$]

[Chem. 36]

formula (b)

[Chemical structure: naphthalene ring with substituents $A_4$, $X_2$, $A_3$, CHO, $A_2$, SMe, $A_1$, $X_1$]

(wherein each of $A_1$ to $A_4$, $X_1$ and $X_2$ is independently selected from the group consisting of a hydrogen atom, a halogen atom, an alkyl group and the like, and two adjacent members out of $A_1$ to $A_4$ may combine with each other to form a substituted or unsubstituted aromatic group having from 4 to 20 carbon atoms).

The reduction above can be performed by any reducing agent capable of reducing the cyano group (—CN) of the compound of formula (i) to an aldehyde group (—CHO).

As this reducing agent, a boron compound such as borane and diborane; a metal hydride such as hydrazine, diisobutylaluminum hydride, lithium aluminum hydride, sodium boron hydride and lithium boron hydride; and a combination of a metal hydride and a Lewis acid, and particularly diisobutylaluminum hydride (DIBAL), may be considered.

Also, the temperature, time and amount of reducing agent for the reduction may be selected so that the intended reduction reaction can be achieved. For example, in the case of using diisobutylaluminum hydride as the reducing agent, a reaction temperature of −100 to 25° C., particularly from −80 to 0° C., and more particularly from −78 to −50° C., may be considered.

In addition, the reduction reaction can be performed in a solvent that does not inhibit the reduction reaction. As this solvent, a chlorine-based solvent such as methylene chloride, chloroform and trichloroethylene; a hydrocarbon-based solvent such as hexane, heptane, benzene, toluene, xylene and cumene; an ether-based solvent such as dibutyl ether and diethylene glycol diethyl ether, may be considered.

<Synthesis of Compound of Formula (i)>

The method of the fourth aspect of the present invention for synthesizing the compound of formula (b) may comprise substituting the triflate group of a compound of formula (g) by a cyano group to synthesize the compound of formula (i):

[Chem. 37]

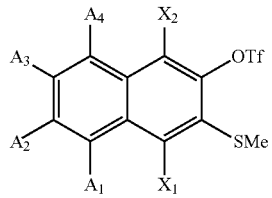

formula (g)

The cyanidation reaction above can be performed by any cyanide capable of substituting a cyano group (—CN) for the triflate group (—OTf) of the compound of formula (g)

As this cyanide, a hydrogen cyanide, a metal cyanide, a cyanhydrin compound, an acyl cyanide, and a cyan halide may be considered. Specific metal cyanides which can be considered are a cyanide of an alkali metal, such as sodium cyanide and potassium cyanide; a cyanide of an alkaline earth metal, such as calcium cyanide; and a cyanide of a transition metal, such as copper cyanide. Also, as the cyanhydrin compound, an α-cyanhydrin compound such as hydroxyacetonitrile, lactonitrile and acetone cyanhydrin may be considered. As the acyl cyanide, an aliphatic acyl cyanide such as acetyl cyanide and propionyl cyanide; and an aromatic acyl cyanide such as benzoyl cyanide may be considered. Furthermore, as the cyan halide, cyan chloride and cyan bromide may be considered.

For the cyanidation reaction, an activator capable of accelerating the reaction by capturing the desorbed triflate group (—OTf) can be added. As this activator, tetra-n-butyl ammonium:iodide may be considered.

The cyanidation reaction above can be accelerated by a transition metal catalyst, particularly a noble metal catalyst, and more particularly a palladium catalyst. As this catalyst, a combination of 1,1'-bis(diphenylphosphino)ferrocene (DPPF) and bis(dibenzylideneacetone)palladium may be considered.

<Synthesis of Compound of Formula (g)>

As for the synthesis of the compound of formula (g), Non-Patent Document 4 may be referred to, and specifically, the compound can be synthesized, for example, by a reaction illustrated below.

[Chem. 38]

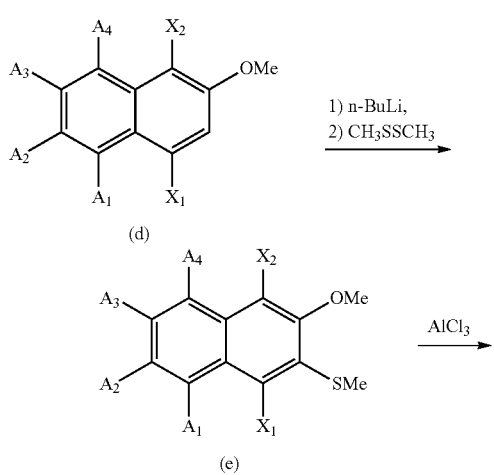

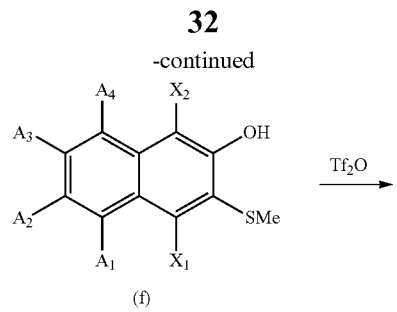

As the compound of formula (d) that is a starting raw material in the reaction formula above, various commercial products are available.

Incidentally, in the reaction formula above, the reaction for synthesizing formula (e) from the compound of formula (d) uses n-butyllithium (n-BuLi) as a strong base for extracting hydrogen on the 3-position of the naphthalene ring, but other strong bases, for example, other alkyllithiums, may also be considered.

Fifth Aspect of the Present Invention

Synthesis Method 2 of Intermediate

The method of the fifth aspect of the present invention for synthesizing a compound of the following formula (b), i.e. the method of the fifth aspect of the present invention for synthesizing a compound of the following formula (b) usable as an intermediate for the synthesis of DNTT or a derivative thereof, comprises partially oxidizing the hydroxyl group of a compound of the following formula (n) to an aldehyde group:

[Chem. 39]

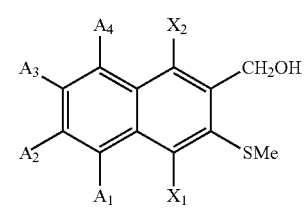

formula (n)

[Chem. 40]

formula (b)

(wherein each of $A_1$ to $A_4$, $X_1$ and $X_2$ is independently selected from the group consisting of a hydrogen atom, a halogen atom, an alkyl group and the like, and two adjacent members out of $A_1$ to $A_4$ may combine with each other to form a substituted or unsubstituted aromatic group having from 4 to 20 carbon atoms).

The oxidation above can be performed by any oxidizing agent capable of partially oxidizing the hydroxyl group (—OH) of a compound of formula (n) to an aldehyde group (—CHO).

This oxidation can be achieved, for example, by a reaction known as a Swern oxidation reaction, i.e. an alcohol oxidation reaction using dimethylsulfoxide (DMSO) as an oxidizing agent. In such an oxidation reaction, oxalyl chloride, acetic anhydride, $SO_3$-pyridine, dichlorohexylcarbodiimide and the like can be used as an activator. Also, triethylamine, trifluoroacetic acid or the like may be used in combination, if desired.

The temperature, time and solvent for the oxidation reaction may be selected so that the intended oxidation reaction can be achieved. For example, as the solvent for the oxidation reaction, solvents recited as a solvent when reducing the compound of formula (i) to the compound of formula (b), i.e. methylene chloride and the like, may be considered.

<Synthesis of Compound of Formula (n)>

Also, the method of the fifth aspect of the present invention for synthesizing the compound of formula (b) may comprise reducing the ester group of a compound of formula (m) to a hydroxyl group to synthesize the compound of formula (n):

[Chem. 41]

formula (m)

(wherein R is selected from the group consisting of an alkyl group and the like).

The reduction above can be performed by any reducing agent capable of reducing the ester group (—COOR) of a compound of formula (m) to a hydroxyl group (—OH).

As this reducing agent, reducing agents used when reducing the compound of formula (i) to the compound of formula (b), and particularly strong reducing agents such as lithium aluminum hydride, may be considered. Also, the temperature, time and solvent for the reduction reaction may be selected so that the intended oxidation reaction can be achieved. With respect to these conditions, the conditions when reducing the compound of formula (i) to the compound of formula (b) may be considered.

<Synthesis of Compound of Formula (m)>

Also, the method of the fifth aspect of the present invention for synthesizing the compound of formula (b) may comprise substituting the triflate group of a compound of formula (l) by a thiomethyl group to synthesize the compound of formula (m):

[Chem. 42]

formula (l)

The substitution reaction above can be performed by any thiomethoxide compound capable of substituting a thiomethyl group (—$SCH_3$) for the triflate group (—OTf) of the compound of formula (l).

As this thiomethoxide compound, an alkali metal thiomethoxide, and particularly sodium thiomethoxide, may be considered.

<Synthesis of Compound (l)>

Also, the method of the fifth aspect of the present invention for synthesizing the compound of formula (b) may comprise substituting the hydroxy group of a compound of formula (k) by a triflate group to synthesize the compound of formula (l):

[Chem. 43]

formula (k)

The substitution reaction above can be performed by any triflate compound capable of substituting a triflate group (—OTf) for the hydroxyl group (—OH) of the compound of formula (k).

As this triflate compound, a trifluoromethesulfonic acid anhydride may be considered. Furthermore, the substitution reaction may also be accelerated using pyridine, 4,4-dimethylaminopyridine (DMAP) or the like.

Incidentally, as the compound of formula (k) used as a raw material in the reaction above, various products are commercially available.

<<Synthesis Method of DNTT, etc. from Intermediate>>

The method of the present invention for synthesizing a compound of the following formula (x) comprises synthesizing the compound of formula (b) by the method of the fourth or fifth aspect of the present invention and condensing two molecules of the compound of formula (b):

[Chem. 44]

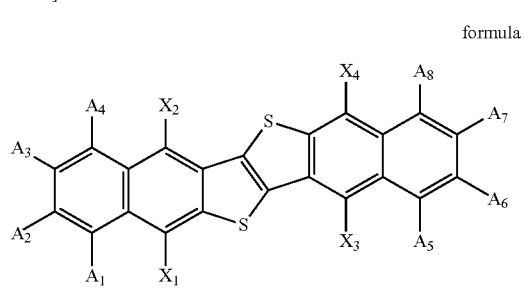

formula (x)

(wherein each of $A_1$ to $A_8$ and $X_1$ to $X_4$ is independently selected from the group consisting of a hydrogen atom, a halogen atom, an alkyl group and the like, and two adjacent members out of $A_1$ to $A_8$ and $X_1$ to $X_4$ may combine with each other to form a substituted or unsubstituted aromatic group having from 4 to 20 carbon atoms).

As for the synthesis of the compound of formula (x) from the compound of formula (b), Patent Document 2 and the like may be referred to, and specifically, the compound can be synthesized, for example, by a reaction illustrated below.

[Chem. 45]

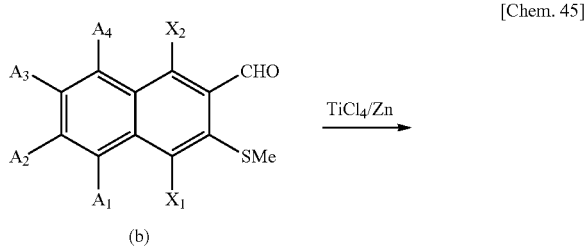

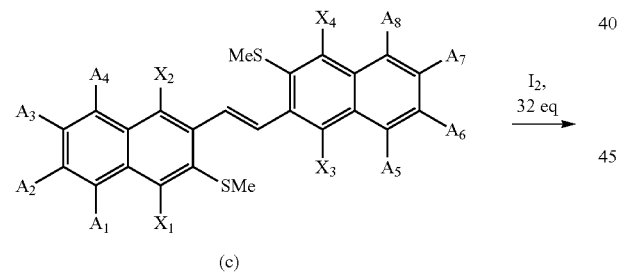

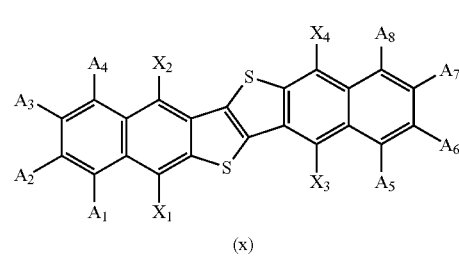

Accordingly, for example, in the case of using the method of the fourth aspect of the present invention for synthesizing a compound of formula (b), in the method of the present invention for synthesizing DNTT, the DNTT can be synthesized by the following route.

[Chem. 46]

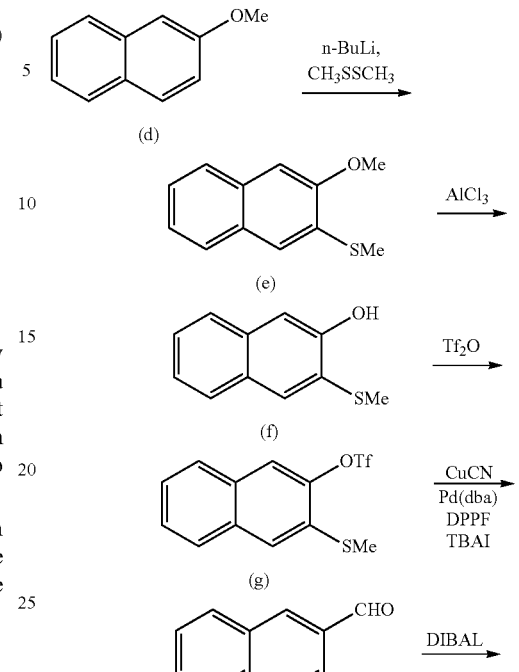

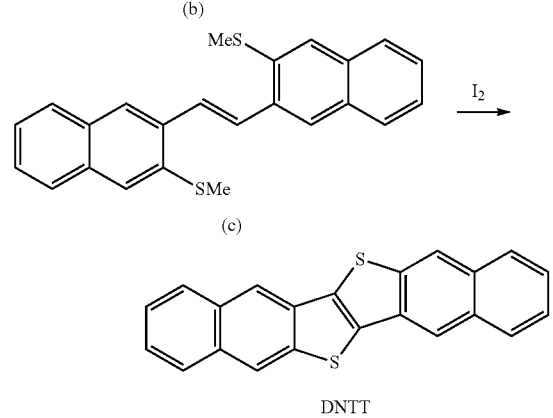

Also, for example, in the case of using the method of the fifth aspect of the present invention for synthesizing a compound of formula (b), in the method of the present invention for synthesizing DNTT, the DNTT can be synthesized by the following route.

[Chem. 47]

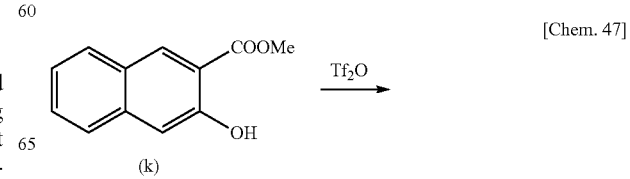

-continued

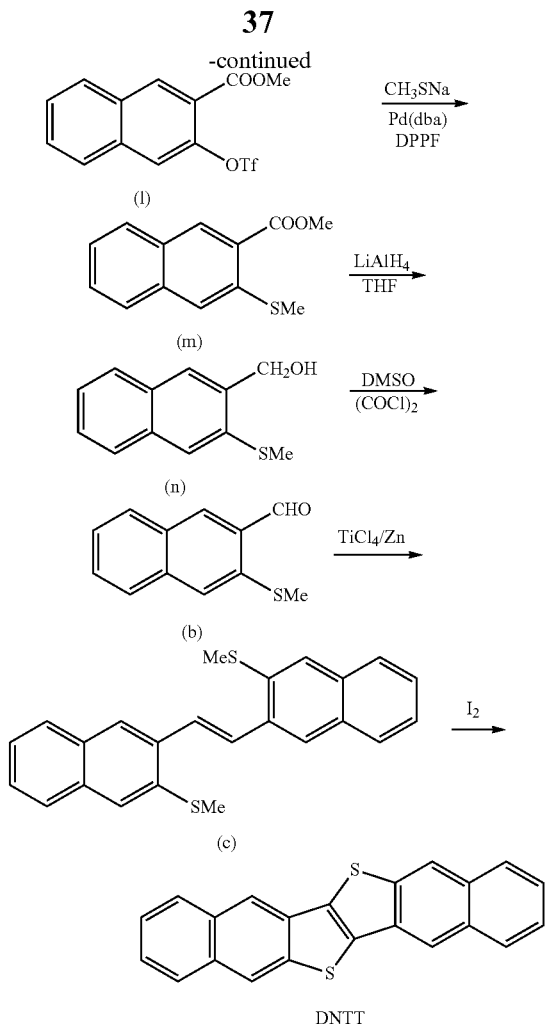

EXAMPLES

In the following Examples, the structure of the target compound was determined as needed by 1H-nuclear magnetic resonance spectrum (1H-NMR spectrum), mass spectrometry (MS), single-crystal structural analysis and gel permeation chromatography (GPC).

The devices used are as follows.

1H-NMR (Examples A and B): ECA-500 of JEOL (500 MHz)
1H-NMR (Example C): AVANCE 500 of BLUKER
MS (Examples A and B): Autoflex III (MALDI) of Bruker
Single crystal structural analysis (Example A):
   RAXIS RAPID S of Rigaku
GPC (Example A):
   LC-9101 of Japan Analytical Industry Co., Ltd. (column: JAIGEL-2H, JAIGEL-1H)
GPC (Example B):
   LC-9101 of Japan Analytical Industry Co., Ltd. (column: JAIGEL-6H, JAIGEL-5H)

First and Second Aspects of the Present Invention

Example A-1

Dinaphthothienothiophene (DNTT) (structural formula shown below, MW=340.46) was synthesized by the method described in Patent Document 2 (Kokai No. 2008-290963 (Nippon Kayaku Co., Ltd., Hiroshima University)).

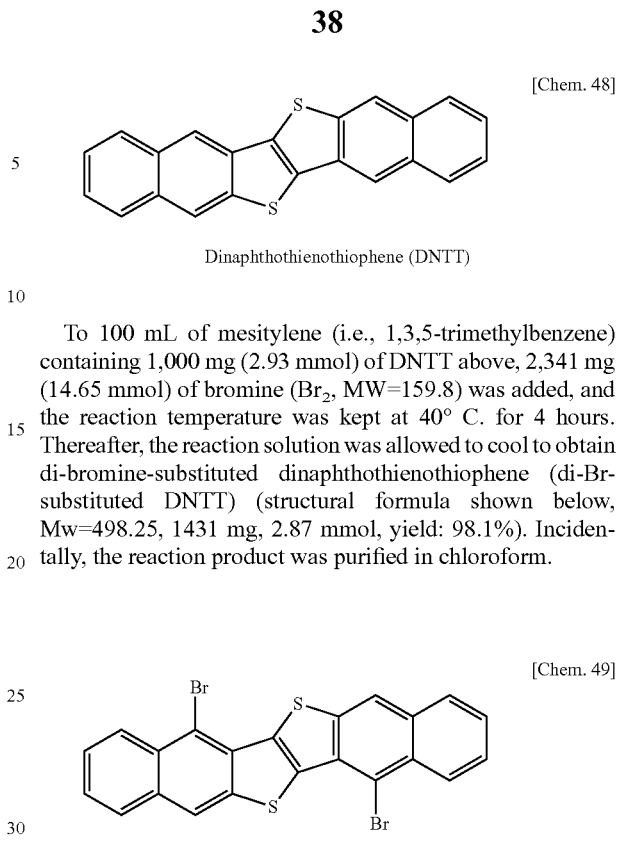

Dinaphthothienothiophene (DNTT)

To 100 mL of mesitylene (i.e., 1,3,5-trimethylbenzene) containing 1,000 mg (2.93 mmol) of DNTT above, 2,341 mg (14.65 mmol) of bromine ($Br_2$, MW=159.8) was added, and the reaction temperature was kept at 40° C. for 4 hours. Thereafter, the reaction solution was allowed to cool to obtain di-bromine-substituted dinaphthothienothiophene (di-Br-substituted DNTT) (structural formula shown below, Mw=498.25, 1431 mg, 2.87 mmol, yield: 98.1%). Incidentally, the reaction product was purified in chloroform.

Di-bromine-substituted dinaphthothienothiophene (di-Br-substituted DNTT)

Incidentally, the substitution position of bromine in the di-Br-substituted DNTT was judged from the position of the triisopropylsilyl (TIPS) group by single-crystal structural analysis of di-TIPS-substituted DNTT in Example A-2.

The $^1$H-NM and MS results of the obtained di-Br-substituted DNTT are shown below.

$^1$H-NMR (500 MHz, $CDCl_3$, 50° C.): δ8.47 (d, J=8.3 Hz, 2H), 8.44 (s, 2H), 7.97 (d, J=8.3 Hz, 2H), 7.66 (t, J=8.3 Hz, 2H), 7.59 (t, J=8.3 Hz, 2H).

MS (m/z): 497.513 (positive ion observation) (Exact Mass: 495.86).

Example A-1A

To a flask, 100.7 mg (0.296 mmol) of DNTT synthesized as in Example A-1A and 17.7 mg (0.133 mmol) of aluminum chloride were added, and nitrogen purging was performed three times. Thereafter, 5.0 ml of chloroform was added and after cooling to 0° C., 78.7 mg (0.589 mmol) of N-chlorosuccinimide was added, followed by stirring for 1.5 hours.

After confirming that N-chlorosuccinimide as a raw material disappeared by mass spectrometry (MS), 5.0 ml of water was added to terminate the reaction. The reaction product was filtered to obtain di-chlorine-substituted dinaphthothienothiophene (di-$C_1$-substituted DNTT) (structural formula shown below, Mw=409.35, 116.0 mg, 0.28 mmol, yield: 95.8%). Incidentally, the reaction product was purified in chloroform.

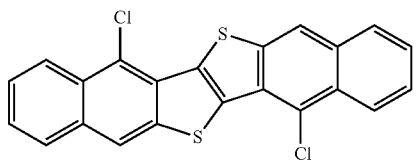

Di-chlorine-substituted dinaphthothienothiophene (di-$C_1$-substituted DNTT)

The MS result of the obtained di-$C_1$-substituted DNTT is shown below.

MS (m/z): 407.822 (positive ion observation) (Exact Mass: 407.96).

Example A-2

The di-Br-substituted DNTT synthesized in Example A-1 was subjected to introduction of a triisopropylsilyl (TIPS) group by the Sonogashira coupling method.

Specifically, 191.3 mg of Pd(PPh$_3$)$_2$Cl$_2$ (Mw=701.90), 134.1 mg of CuI (Mw=190.45), 0.706 mL of diisopropylamine (Mw=101.20), 791.6 mg of CsCO$_3$ (Mw=325.82) and 1.698 mL of triisopropylsilylacetylene (Mw=182.38) were added to 500 mg (1.0 mmol) of di-Br-substituted DNTT (Mw=498.25), and deaeration under reduced pressure and nitrogen purging were performed three times. Thereafter, 35 mL of N,N-dimethylformamide (N,N-DMF) was introduced and after again performing deaeration under pressure and nitrogen purging three times, the system was stirred at 120° C. over 20 hours, thereby allowing the reaction to proceed.

By this reaction, 479.1 mg (68.3 mmol, yield: 68.0%) of di-triisopropylsilylacetylene-substituted dinaphthothienothiophene (di-TIPS-substituted DNTT, structural formula shown below) (Mw=701.19) was obtained. The solubility of the obtained di-TIPS-substituted DNTT in chloroform was 0.2 wt %. Incidentally, DNTT used as a raw material was substantially not dissolved in chloroform.

The single crystal structural analysis results of the obtained di-TIPS-substituted DNTT are shown below.

a=8.2044 (5) Å
b=8.4591 (6) Å
c=14.488 (1) Å
α=88.475 (4)°
β=89.336 (3)°
γ=89.555 (4)°
v=1005.1 (1) Å$^3$

Figure 2:
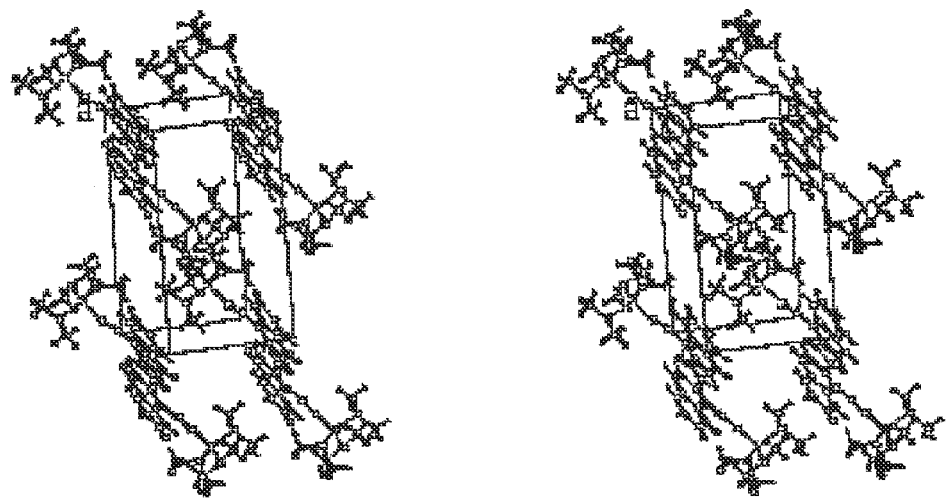
FIG. 2 A crystal packing (stereo) diagram of di-TIPS-substituted DNTT obtained in Example A-2.

Also, the molecular structure ORTEP (Oak Ridge Thermal Ellipsoid Plot) drawing based on single-crystal structural analysis and the crystal packing (stereo) diagram of this di-TIPS-substituted DNTT are depicted in FIGS. 1 and 2, respectively.

Example A-2A

The di-triisopropylsilylacetylene-substituted DNTT (di-TIPS-substituted DNTT) synthesized in Example A-2 was hydrogen-reduced to synthesize di-triisopropylsilylethane-substituted DNTT.

Specifically, to a 200-ml flask, 304.6 mg (0.43 mmol) of di-triisopropylsilylacetylene-substituted DNTT (Mw=701.18), 60 ml of toluene and 79.2 mg of 10% Pd/C were added, and purging with hydrogen was performed three times. The system was stirred at 60° C. for 15 hours in a hydrogen atmosphere, thereby allowing the reaction to proceed.

By this reaction, di-triisopropylsilylethane-substituted DNTT (structural formula shown below, Mw=709.37, 296.1 mg, 0.42 mmol, yield: 96.1%) was obtained. The solubility of the obtained di-triisopropylsilylethane-substituted DNTT in chloroform was 0.51 wt %. Incidentally, DNTT used as a raw material was substantially not dissolved in chloroform.

[Chem. 51]

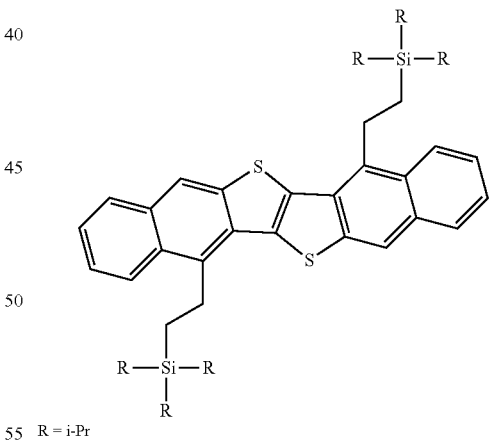

[Chem. 52]

$R_i$: isopropyl (i-Pr)
Di-triisopropylsilylacetylene-substituted dinaphthothienothiophene (di-TIPS-substituted DNTT)

The $^1$H-NMR and MS results of the obtained di-TIPS-substituted DNTT are shown below.

$^1$H-NMR (500 MHz, CDCl$_3$): δ8.61 (d, J=8.0 Hz, 2H), 8.41 (s, 2H), 7.97 (d, J=8.0 Hz, 2H), 7.63 (dd, J=8.0 Hz, 8.0 Hz 2H), 7.57 (dd, J=8.0 Hz, 8.0 Hz, 2H), 1.40-1.47 (m, 6H), 1.34 (d, J=6.9 Hz, 36H)

MS (m/z): 700.3 (Exact Mass: 700.30)

Di-triisopropylsilylethane-substituted DNTT (di-TIPS4H2-substituted DNTT)

The $^1$H-NMR and MS results of the obtained di-triisopropylsilylethane-substituted DNTT are shown below.

$^1$H-NMR (500 MHz, CDCl$_3$, 50° C.): δ8.33 (s, 2H), 7.26 (d, J=8.6 Hz, 2H), 7.97 (d, J=8.6 Hz, 2H), 7.57 (dd, J=8.6 Hz, 8.6 Hz, 2H), 7.53 (dd, J=8.3 Hz, 8.3 Hz, 2H), 3.76-3.72 (m, 8H), 1.39-1.32 (m, 6H), 1.30-1.19 (m, 36H).

MS (m/z): 708.322 (positive ion observation) (Exact Mass: 708.367).

Example A-3

Di-TIPS-substituted DNTT (Mw=701.19) obtained in Example A-2 was dissolved in chloroform at a concentration of 0.2 wt % to prepare a solution for the manufacture of a semiconductor device.

Next, an n-doped silicone wafer with an SiO$_2$ oxide film of 300 nm (surface resistance: $1^{-10}$ Ω·cm) was subjected to a UV-ozone treatment for 20 minutes (Eye UV-Ozone Cleaning System OC-250615-D+A, Eye Graphics Co., Ltd.). Also, a toluene solution containing 10 mmol of 1,1,1,3,3,3-hexamethyldisilazane (HMDS) was prepared, and the silicon substrate subjected the UV ozone treatment was dipped in this solution over 24 hours, thereby performing a hydrophobing treatment of the silicon substrate. Thereafter, source/drain gold electrodes having a channel width of 50 μm and a channel length of 1.5 mm were produced by the vacuum deposition method (resistance-heating vapor deposition apparatus: SVC-700 TM/700-2, Sanyu Electron Co., Ltd.).

While heating the silicon substrate at 40° C., the solution for the manufacture of a semiconductor device was dropped on the channel portion to volatilize the solvent, and thereby form a thin layer composed of di-TIPS-substituted DNTT. The thus-produced device was heat-treated at 70° C. over 1 hour in a vacuum to dry and remove the chloroform solvent and thereby manufacture an organic semiconductor device.

Figure 3:
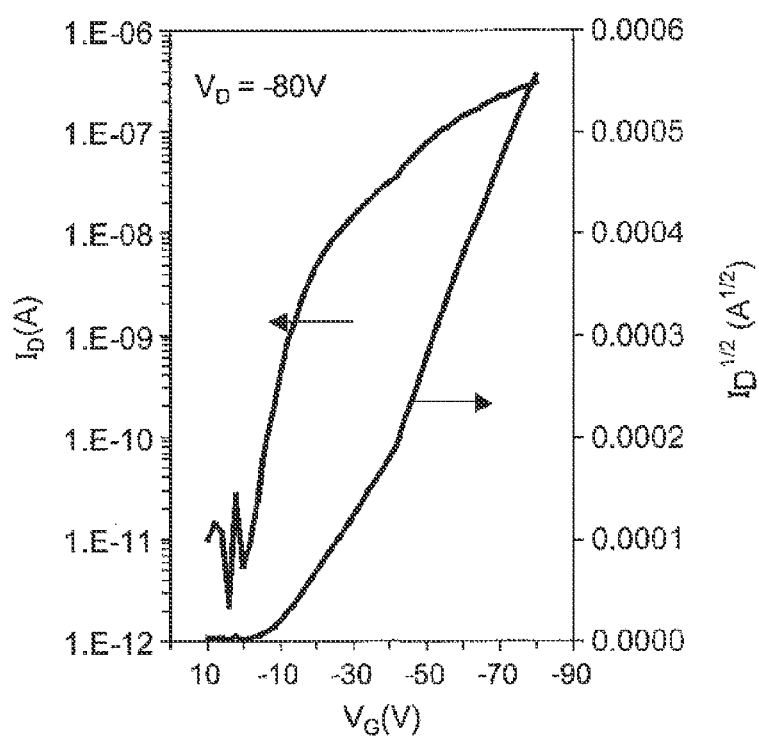
FIG. 3 A view illustrating the transmission property of FET characteristics of the organic semiconductor device obtained in Example A-3.

The obtained organic semiconductor device was measured for the organic semiconductor characteristics and found to exhibit p-type semiconductor behavior. Also, in this organic semiconductor device, the carrier mobility was $1 \times 10^{-3}$ cm$^2$/Vs, the on/off ratio was $10^5$, and the threshold voltage was −26 V. FIG. 3 illustrates the transmission property of FET characteristics. FIG. 3 shows the relationship between the drain current ($I_D$(A) or $I_D^{1/2}$ (A$^{1/2}$)) (ordinate) and the gate voltage ($V_G$(V)) (abscissa) when the drain voltage ($V_D$) is −80 V.

Example A-4

Dinaphthothienothiophene (DNTT) (MW=340.46) was synthesized in the same manner as in Example A-1.

To 500 mL of mesitylene (i.e., 1,3,5-trimethylbenzene) containing 5,000 mg (14.65 mmol) of DNTT above, 12.68 g (73.25 mmol) of N-phenylmaleimide (MW=173.17) was added, and the reaction temperature was kept at 160° C. for 4 hours. Thereafter, the system was allowed to cool and through separation and purification, 376 mg (0.73 mmol, yield: 4.9%) of dinaphthothienothiophene-N-phenylmaleimide monoadduct in which one N-phenylmaleimide was added to DNTT (DNTT-PMI monoadduct, a mixture of Endo form and Exo form which are stereoisomers) (structural formula shown below, Mw=513.63) was obtained. Incidentally, stereoisomers were separated by HPLC to obtain 132 mg of Endo form and 151 mg of Exo form.

[Chem. 53]

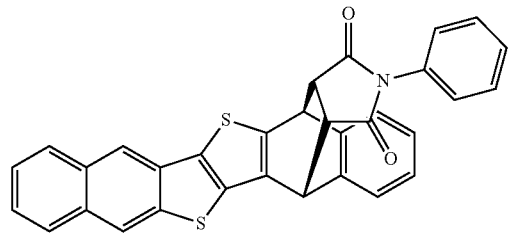

Dinaphthothienothiophene-phenylmaleimide monoadduct (Exo form) (DNTT-PMI monoadduct (Exo form))

[Chem. 54]

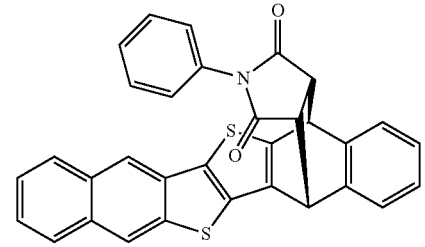

Dinaphthothienothiophene-phenylmaleimide monoadduct (Endo form) (DNTT-PMI monoadduct (Endo form))

To 50 mL of mesitylene containing 151 mg (0.29 mmol) of the DNTT-PMI monoadduct (Exo form) above, 235 mg (1.47 mmol) of bromine (Br$_2$, MW=159.8) was added, and the reaction temperature was kept at 40° C. for 1 hour. Thereafter, the system was allowed to cool, as a result, 186 mg (0.276 mmol, yield: 95.2%) of di-bromine-substituted dinaphthothienothiophene-N-phenylmaleimide monoadduct (di-Br-substituted DNTT-PMI monoadduct) (structural formula shown below, Mw=673.44) was obtained.

[Chem. 55]

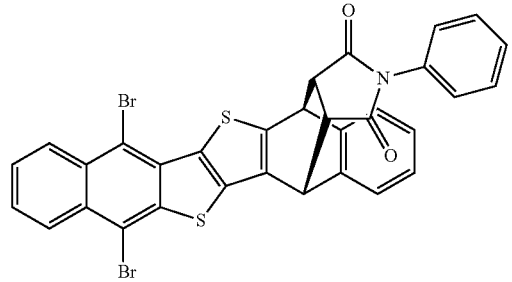

Di-bromine-substituted dinaphthothienothiophene-phenylmaleimide monoadduct (Exo form) (di-Br-substituted DNTT-PMI monoadduct (Exo form))

The $^1$H-NMR and MS results of the obtained di-Br-substituted DNTT-PMI monoadduct are shown below.

$^1$H-NMR (500 MHz, CDCl$_3$): δ8.39 (d, J=7.7 Hz, 1H), 8.29 (d, J=7.7 Hz, 1H), 7.67 (dd, J=7.7 Hz, 1H), 7.64 (dd, J=7.7 Hz, 1H), 7.41-7.44 (m, 2H), 7.31-7.32 (m, 3H), 7.27-7.29 (m, 2H), 6.52-6.54 (m, 2H), 5.25 (d, J=3.2 Hz, 1H), 5.23 (d, J=3.2 Hz, 1H), 3.59 (dd, J=3.2 Hz, 8.3 Hz, 1H), 3.55 (dd, J=3.2 Hz, 8.3 Hz, 1H).

MS (m/z): 497.513 (Exact Mass: 670.92)

Incidentally, it is presumed that in MS, di-Br-substituted DNTT (Exact Mass: 497.86) formed as a result of desorption of N-phenylmaleimide from the di-Br-substituted DNTT-PMI monoadduct was observed.

Example A-5

The di-Br-substituted DNTT-PMI monoadduct synthesized in Example A-4 was subjected to introduction of a triisopropylsilyl (TIPS) group by the Sonogashira coupling method.

Specifically, 28.1 mg of $Pd(PPh_3)_2Cl_2$ (Mw=701.90), 20.0 mg of CuI (Mw=190.45), 0.11 mL of diisopropylamine (Mw=101.20) and 0.1 mL of triisopropylsilylacetylene (Mw=182.38) were added to 100 mg (0.148 mmol) of di-Br-substituted DNTT-PMI monoadduct (Mw=673.44), and deaeration under reduced pressure and nitrogen purging were performed three times. Thereafter, 7 mL of N,N-dimethylformamide (N,N-DMF) was introduced and after again performing deaeration under pressure and nitrogen purging three times, the system was stirred at 120° C. over 20 hours, thereby allowing the reaction to proceed.

By this reaction, 74.9 mg (85.4 mmol, yield: 57.7%) of di-triisopropylsilylacetylene-substituted dinaphthothienothiophene-phenylmaleimide monoadduct (exo form) (di-TIPS-substituted DNTT-PMI monoadduct (exo form)) (structural formula shown below, Mw=876.37) was obtained.

[Chem. 56]

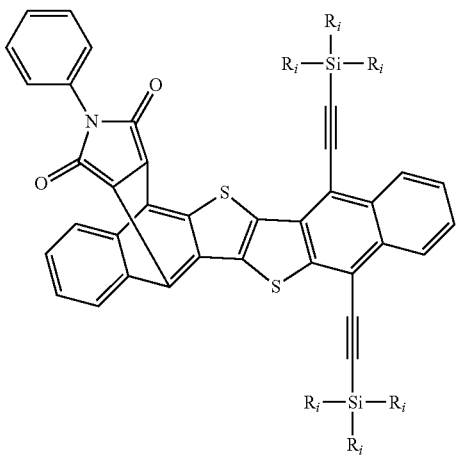

$R_i$: isopropyl (i-Pr)

Di-triisopropylsilylacetylene-substituted dinaphthothienothiophene-phenylmaleimide monoadduct (exo form) (di-TIPS-substituted DNTT-PMI monoadduct (exo form))

The $^1$H-NMR and MS results of the obtained di-TIPS-substituted DNTT-PMI monoadduct (exo form) are shown below.

$^1$H-NMR (500 MHz, CDCl$_3$): δ8.52-8.54 (m, 1H), 8.43-8.45 (m, 1H), 7.60-7.64 (m, 2H), 7.43-7.46 (m, 2H), 7.31-7.33 (m, 3H), 7.25-7.29 (m, 2H), 6.52-6.54 (m, 2H), 5.29 (d, J=3.4 Hz, 1H), 5.21 (d, J=3.4 Hz, 1H), 3.62 (dd, J=3.4 Hz, 8.3 Hz, 1H), 3.56 (dd, J=3.4 Hz, 8.3 Hz, 1H), 1.36-1.43 (m, 6H), 1.31 (d, J=2.9 Hz, 12H), 1.30 (d, J=4.0 Hz, 24H)

MS (m/z): 873.078 (Exact Mass: 875.37).

Example A-6

The di-Br-substituted DNTT synthesized in Example A-1 was reacted with 1-decyne by the Sonogashira coupling method to synthesize di-1-decyne-substituted DNTT.

Specifically, 761.1 mg (1.08 mmol) of $Pd(PPh_3)_2Cl_2$ (Mw=701.90), 577 mg (3.03 mmol) of CuI (Mw=190.45) and 3.20 g (9.82 mmol) of $Cs_2CO_3$ (Mw=325.8) were added to 1000 mg (2.01 mmol) of di-Br-substituted DNTT (Mw=498.25), and deaeration under reduced pressure and nitrogen purging were performed five times.

Thereafter, 70 ml of dimethylformamide, 1.41 ml (10.0 mmol) of diisopropylamine (Mw=101.2, d=0.72 g/cm$^3$) and 2.78 ml (15.4 mmol) of 1-decyne (Mw=138.25, d=0.77 g/cm$^3$) were added and after again performing deaeration under reduced pressure and nitrogen purging five times, the system was stirred at 120° C. over 15.5 hours, thereby allowing the reaction to proceed.

By this reaction, di-1-dysine-substituted DNTT (structural formula shown below, Mw=612.93, 20.5 mg, 0.033 mmol, yield: 1.6%) was obtained. The solubility of the obtained di-1-dysine-substituted DNTT in chloroform was 2.3 wt %. Incidentally, DNTT used as a raw material was substantially not dissolved in chloroform.

[Chem. 57]

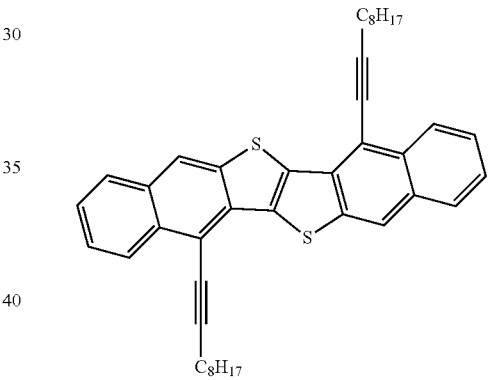

Di-1-dysine-substituted dinaphthothienothiophene (di-1-dysine-substituted DNTT)

The $^1$H-NMR and MS results of the obtained di-1-dysine-substituted DNTT are shown below.

$^1$H-NMR (500 MHz, CDCl$_3$, 50° C.): 88.45 (d, J=8.3 Hz, 2H), 8.25 (s, 2H), 7.86 (d, J=8.3 Hz, 2H), 7.54 (dd, J=8.3 Hz, 6.9 Hz, 2H), 7.48 (dd, J=8.3 Hz, 6.9 Hz, 2H), 2.81 (t, J=7.2 Hz, 4H), 1.90 (tt, J=7.2 Hz, 7.2 Hz, 4H), 1.65 (tt, J=7.2 Hz, 7.2 Hz, 4H), 1.31-1.48 (m, 16H), 0.89 (t, J=7.2 Hz, 6H).

MS (m/z): 612.284 (positive ion observation) (Exact Mass: 612.288).

Example A-7

The di-Br-substituted DNTT synthesized in Example A-1 was reacted with 1-tetradecyne by the Sonogashira coupling method to synthesize di-1-tetradecyne-substituted DNTT.

Specifically, 830.0 mg (1.17 mmol) of $Pd(PPh_3)_2Cl_2$ (Mw=701.90), 590.0 mg (3.12 mmol) of CuI (Mw=190.45) and 1.62 g (4.98 mmol) of $Cs_2CO_3$ (Mw=325.8) were added to 1000 mg (2.01 mmol) of di-Br-substituted DNTT (Mw=498.25), and deaeration under reduced pressure and nitrogen purging were performed five times.

Thereafter, 70 ml of dimethylformamide, 1.41 ml (10.0 mmol) of diisopropylamine (Mw=101.2, d=0.72 g/cm$^3$) and 4.19 ml (17.0 mmol) of 1-tetradecyne (Mw=194.36, d=0.79 g/cm$^3$) were added and after again performing deaeration under reduced pressure and nitrogen purging five times, the system was stirred at 120° C. over 12 hours, thereby allowing the reaction to proceed.

By this reaction, di-1-tetradysine-substituted DNTT (structural formula shown below, Mw=612.93, 156.04 mg, 0.207 mmol, yield: 10.3%) was obtained. The solubility of the obtained di-1-tetradysine-substituted DNTT in chloroform was 6.5 wt %. Incidentally, DNTT used as a raw material was substantially not dissolved in chloroform.

[Chem. 58]

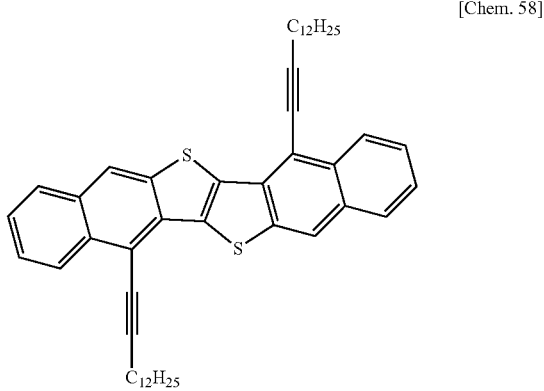

The $^1$H-NMR and MS results of the obtained di-1-tetradysine-substituted DNTT are shown below.

$^1$H-NMR (500 MHz, CDCl$_3$, 50° C.): δ8.38 (d, J=8.3 Hz, 2H), 8.14 (s, 2H), 7.78 (d, J=8.3 Hz, 2H), 7.48 (dd, J=8.3 Hz, 6.6 Hz, 2H), 7.42 (dd, J=8.3 Hz, 6.6 Hz, 2H), 2.76 (t, J=7.2 Hz, 4H), 1.86 (tt, J=7.2 Hz, 7.2 Hz, 4H), 1.62 (tt, J=7.2 Hz, 7.2 Hz, 4H), 1.24-1.46 (m, 32H), 0.86 (t, J=7.2 Hz, 6H).

MS (m/z): 724.411 (positive ion observation) (Exact Mass: 724.414).

Example A-7A

The di-Br-substituted DNTT synthesized in Example A-1 was reacted with 1-tetradecyne by using Negishi coupling in place of the Sonogashira coupling method used in Example A-7 to synthesize di-1-tetradecyne-substituted DNTT.

Specifically, to a 10-ml flask, 0.21 ml (0.85 mmol) of 1-tetradesyne (Mw=194.36, d=0.79 g/cm$^3$) and 3.5 ml of toluene were added, and deaeration under reduced pressure and nitrogen purging were performed three times. After cooling to 0° C., 0.53 ml (0.859 mmol) of a hexane solution of n-BuLi was added and then, the temperature was raised to room temperature.

Thereafter, 215.3 mg (0.853 mmol) of ZnCl$_2$ (TMEDA) (Mw=252.50), 50 mg (0.10 mmol) of di-Br-substituted DNTT (Mw=498.25) and 35.2 mg (0.05 mmol) of Pd(PPh$_3$)$_2$Cl$_2$ (Mw=701.90) were added, and deaeration under reduced pressure and nitrogen purging were performed three times. The system was stirred at 100° C. over 12 hours, thereby allowing the reaction to proceed.

By this reaction, di-1-tetradesyne-substituted DNTT (structural formula shown above, Mw=612.93, 8.9 mg, 0.012 mmol, yield: 12.2%) was obtained.

Example A-8

The di-Br-substituted DNTT synthesized in Example A-1 was reacted with 1-octadecyne by the Sonogashira coupling method to synthesize di-1-octadecyne-substituted DNTT.

Specifically, 820.0 mg (1.17 mmol) of Pd(PPh$_3$)$_2$Cl$_2$ (Mw=701.90), 590.0 mg (3.12 mmol) of CuI (Mw=190.45) and 1.58 g (4.85 mmol) of Cs$_2$CO$_3$ (Mw=325.8) were added to 1010 mg (2.02 mmol) of di-Br-substituted DNTT (Mw=498.25), and deaeration under reduced pressure and nitrogen purging were performed five times.

Thereafter, 70 ml of dimethylformamide, 1.41 ml (10.0 mmol) of diisopropylamine (Mw=101.2, d=0.72 g/cm$^3$) and 5.34 ml (16.8 mmol) of 1-octadecyne (Mw=250.46, d=0.79 g/cm$^3$) were added and after again performing deaeration under reduced pressure and nitrogen purging five times, the system was stirred at 120° C. over 14 hours, thereby allowing the reaction to proceed.

By this reaction, di-1-octadecyne-substituted DNTT (structural formula shown below, Mw=836.54, 54.2 mg, 0.064 mmol, yield: 3.2%) was obtained.

[Chem. 59]

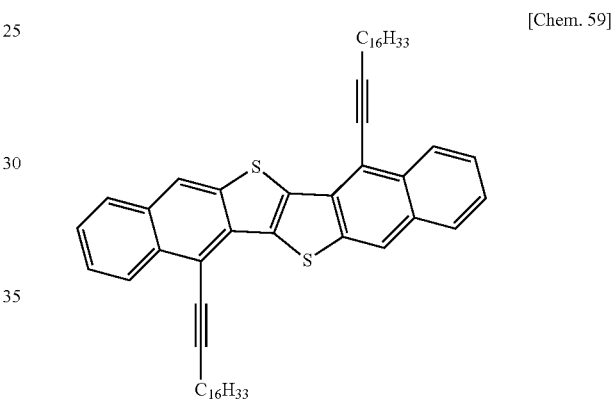

Example A-8A

The di-Br-substituted DNTT synthesized in Example A-1 was reacted with 1-tetradecyne by using Negishi coupling in place of the Sonogashira coupling method used in Example A-8 to synthesize di-1-octadecyne-substituted DNTT.

Specifically, to a 10-ml flask, 0.26 ml (0.85 mmol) of 1-octadesyne (Mw=250.46, d=0.80 g/cm$^3$) and 3.5 ml of toluene were added, and deaeration under reduced pressure and nitrogen purging were performed three times. After cooling to 0° C., 0.53 ml (0.859 mmol) of a hexane solution of n-BuLi was added and then, the temperature was raised to room temperature.

Thereafter, 216.1 mg (0.856 mmol) of ZnCl$_2$ (TMEDA) (Mw=252.50), 49.7 mg (0.10 mmol) of di-Br-substituted DNTT (Mw=498.25) and 35.6 mg (0.05 mmol) of Pd(PPh$_3$)$_2$Cl$_2$ (Mw=701.90) were added, and deaeration under reduced pressure and nitrogen purging were performed three times. The system was stirred at 100° C. over 12 hours, thereby allowing the reaction to proceed.

By this reaction, di-1-octadesyne-substituted DNTT (structural formula shown above, Mw=836.54, 3.8 mg, 0.004 mmol, yield: 4.5%) was obtained. The solubility of the obtained di-1-tetradesyne-substituted DNTT in chloroform was 1.67 wt %. Incidentally, DNTT used as a raw material was substantially not dissolved in chloroform.

The $^1$H-NMR and MS results of the obtained di-1-octadesyne-substituted DNTT are shown below. $^1$H-NMR (500 MHz, CDCl$_3$, 50° C.): δ8.48 (d, J=8.3 Hz, 2H), 8.30 (s, 2H), 7.89 (d, J=8.3 Hz, 2H), 7.56 (dd, J=8.3 Hz, 6.6 Hz, 2H), 7.51 (dd, J=8.3 Hz, 6.6 Hz, 2H), 2.83 (t, J=7.2 Hz, 4H), 1.91 (tt, J=7.2 Hz, 7.2 Hz, 2H), 1.66 (tt, J=7.2 Hz, 7.2 Hz, 2H), 1.24-1.46 (m, 48H), 0.87 (t, J=7.2 Hz, 6H).

MS (m/z): 836.539 (positive ion observation) (Exact Mass: 836.537).

Example A-9

The di-Br-substituted DNTT synthesized in Example 1 was reacted with trimethylsilylacetylene (TMS) by the Negishi coupling method to synthesize di-TMS-substituted DNTT.

To a 200-ml flask, 1.68 g (17.10 mmol) of trimethylsilylacetylene (Mw=98.22, d=0.70 g/cm$^3$) and 70 ml of toluene were added, and deaeration under reduced pressure and nitrogen purging were performed three times. After cooling to 0° C., 10.3 ml (16.68 mmol) of a hexane solution of n-BuLi was added and then, the temperature was raised to room temperature.

Thereafter, 4.31 g (17.06 mmol) of ZnCl$_2$ (TMEDA) (Mw=252.50), 1.0 g (2.00 mmol) of di-Br-substituted DNTT (Mw=498.25) and 702.5 mg (1.00 mmol) of Pd(PPh$_3$)$_2$Cl$_2$ (Mw=701.90) were added, and deaeration under reduced pressure and nitrogen purging were performed three times. The system was stirred at 100° C. over 12 hours, thereby allowing the reaction to proceed.

By this reaction, di-trimethylsilylacetylene-substituted DNTT (di-TMS-substituted DNTT) (structural formula shown above, Mw=532.87, 536.30 mg, 1.00 mmol, yield: 50.1%) was obtained. The solubility of the obtained di-trimethylsilylacetylene-substituted DNTT in chloroform was 0.05 wt %. Incidentally, DNTT used as a raw material was substantially not dissolved in chloroform.

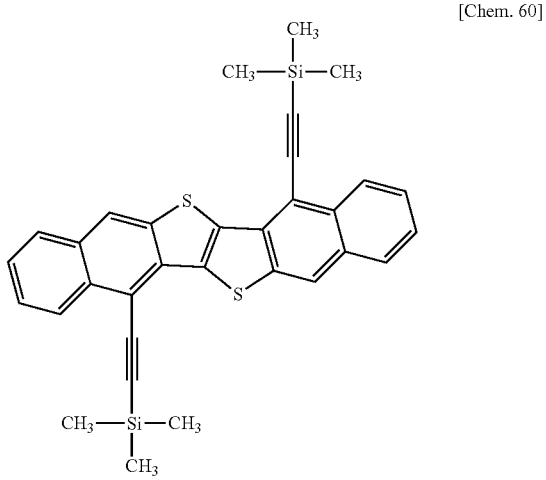 [SMILES: C[Si](C)(C)C#Cc1c2ccccc2cc2sc3c(sc4cc5ccccc5c(C#C[Si](C)(C)C)c43)c12]

[Chem. 60]

Di-trimethylsilylacetylene-substituted DNTT (di-TMS-substituted DNTT)

The $^1$H-NMR and MS results of the obtained di-TMS-substituted DNTT are shown below.

$^1$H-NMR (500 MHz, CDCl$_3$, 50° C.): δ8.53 (d, J=8.3 Hz, 2H), 8.43 (s, 2H), 7.96 (d, J=8.3 Hz, 2H), 7.63 (dd, J=8.3 Hz, 8.3 Hz, 2H), 7.57 (dd, J=8.3 Hz, 8.3 Hz, 2H), 0.52 (s, 18H).

MS (m/z): 532.008 (positive ion observation) (Exact Mass: 532.111).

Example A-10

The di-Br-substituted DNTT synthesized in Example A-1 was reacted with triethylsilylacetylene (TES) by the Negishi coupling method to synthesize di-TES-substituted DNTT.

To a 200-ml flask, 2.25 g (16.03 mmol) of triethylsilylacetylene (Mw=140.30, d=0.78 g/cm$^3$) and 70 ml of toluene were added, and deaeration under reduced pressure and nitrogen purging were performed three times. After cooling to 0° C., 10.3 ml (16.68 mmol) of a hexane solution of n-BuLi was added and then, the temperature was raised to room temperature.

Thereafter, 4.31 g (17.06 mmol) of ZnCl$_2$ (TMEDA) (Mw=252.50), 1.0 g (2.00 mmol) of di-Br-substituted DNTT (Mw=498.25) and 704.8 mg (1.00 mmol) of Pd(PPh$_3$)$_2$Cl$_2$ (Mw=701.90) were added, and deaeration under reduced pressure and nitrogen purging were performed three times. The system was stirred at 100° C. over 12 hours, thereby allowing the reaction to proceed.

By this reaction, di-triethylsilylacetylene-substituted DNTT (di-TES-substituted DNTT) (structural formula shown above, Mw=617.03, 321.40 mg, 0.52 mmol, yield: 26.0%) was obtained. The solubility of the obtained di-triethylsilylacetylene-substituted DNTT in chloroform was 0.10 wt %. Incidentally, DNTT used as a raw material was substantially not dissolved in chloroform.

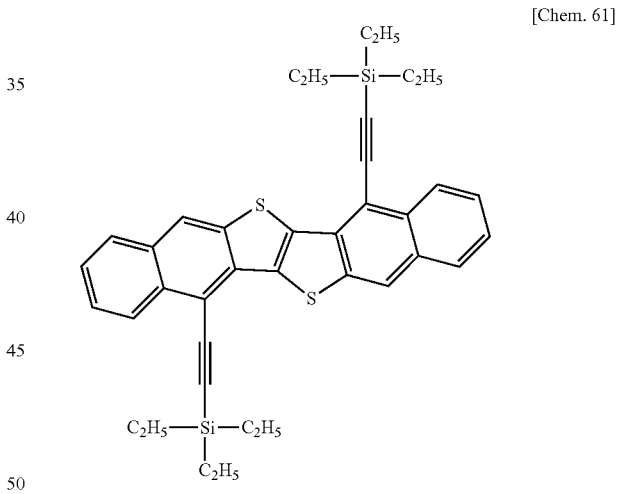

[Chem. 61]

Di-triethylsilylacetylene-substituted DNTT (di-TES-substituted DNTT)

The $^1$H-NMR and MS results of the obtained di-TES-substituted DNTT are shown below.

$^1$H-NMR (500 MHz, CDCl$_3$, 50° C.): 88.56 (d, J=8.3 Hz, 2H), 8.42 (s, 2H), 7.96 (d, J=8.3 Hz, 2H), 7.63 (dd, J=8.3 Hz, 8.3 Hz, 2H), 7.57 (dd, J=8.3 Hz, 8.3 Hz, 2H), 1.25 (t, J=8.0 Hz, 18H), 0.94-0.98 (m, 12H).

MS (m/z): 616.057 (positive ion observation) (Exact Mass: 616.211).

Example A-11

The di-Br-substituted DNTT synthesized in Example A-1 was reacted with thiophene by the Stille coupling method to synthesize di-thiophene-substituted DNTT.

To a 100-ml flask, 500 mg (1.00 mmol) of di-Br-substituted DNTT (Mw=498.25), 351.6 mg (0.501 mmol) of PdCl$_2$(PPh$_3$)$_2$ (Mw=701.90), 3.23 g (8.64 mmol) of tributyl(2-thienyl)tin (Mw=373.18) and 35 ml of dry toluene were added, and nitrogen purging was performed three times. Thereafter, the system was stirred at 100° C. all night.

After confirming that the peak of di-Br-substituted DNTT disappeared from MALDI, the system was cooled to room temperature. Chloroform and water were added, and the precipitate was filtered. The solvent was distilled of from the filtrate, and the peak of the target compound was confirmed by MS only from the filtrate. The black oily substance was washed twice by adding 10 ml of ether thereto, and the solid was filtered to obtain a dark green solid. Thereafter, the dark green solid was purified on a column, and the product was obtained as a yellow solid.

Di-thiophene-substituted DNTT (structural formula shown below, Mw=504.71, 158.80 mg, 0.31 mmol, yield: 31.4%) was obtained. The solubility of the obtained di-triethylsilylacetylene-substituted DNTT in chloroform was 0.13 wt %. Incidentally, DNTT used as a raw material was substantially not dissolved in chloroform.

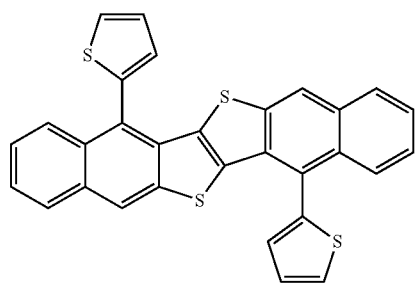

[Chem. 62]

Di-thiophene-substituted DNTT

The $^1$H-NMR and MS results of the obtained di-thiophene-substituted DNTT are shown below.

$^1$H-NMR (500 MHz, CDCl$_3$, 50° C.): 88.31 (s, 2H), 7.92 (d, J=6.5, 2H), 7.87 (d, J=7.0 Hz, 2H), 7.76 (dd, J=1.0 Hz, 1.0 Hz, 2H), 7.52-7.49 (m, 2H), 7.47-7.46 (m, 2H), 7.43-7.41 (m, 2H), 7.28-7.26 (m, 2H).

MS (m/z): 503.838 (positive ion observation) (Exact Mass: 504.013).

Example A-12

The di-Br-substituted DNTT synthesized in Example A-1 was reacted with 1-bromodecane by the Negishi coupling method to synthesize di-decane-substituted DNTT.

Specifically, to a 10-ml flask, 548.2 mg (22.5 mmol) of magnesium was added, and deaeration under reduced pressure and nitrogen purging were performed three times. Thereafter, 2.5 ml of THF and 4.39 ml (21.3 mmol) of 1-bromodecane (Mw=221.18, d=1.07 g/cm$^3$) were added, and refluxing was performed with stirring at 60° C. for 1 hour.

After cooling to room temperature, 100 ml of toluene and 5.32 g (21.31 mmol) of ZnCl$_2$ (TMEDA) (Mw=252.50) were added, followed by stirring for 10 minutes. Thereafter, 1.25 g (2.50 mmol) of di-Br-substituted DNTT (Mw=498.25), 881.5 mg (1.25 mmol) of Pd(PPh$_3$)$_2$Cl$_2$ (Mw=701.90) and 77.5 ml of toluene were added, and deaeration under reduced pressure and nitrogen purging were performed three times. The system was stirred at 100° C. over 12 hours, thereby allowing the reaction to proceed.

By this reaction, di-decane-substituted DNTT (structural formula shown below, Mw=620.99, 44.3 mg, 0.089 mmol, yield: 2.8%) was obtained. The solubility of the obtained di-decane-substituted DNTT in chloroform was 0.05 wt %. Incidentally, DNTT used as a raw material was substantially not dissolved in chloroform.

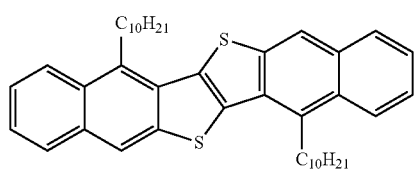

[Chem. 63]

The $^1$H-NMR and MS results of the obtained di-decane-substituted DNTT are shown below.

$^1$H-NMR (500 MHz, CDCl$_3$, 50° C.): δ8.33 (s, 2H), 8.26 (d, J=8.30 Hz, 2H), 7.95 (d, J=8.3 Hz, 2H), 7.56 (dd, J=8.3 Hz, 8.3 Hz, 2H), 7.53 (dd, J=8.3 Hz, 8.3 Hz, 2H), 3.67-3.64 (m, 4H), 1.93-1.86 (m, 4H), 1.76-1.71 (m, 4H), 1.49-1.45 (m, 4H), 1.41-1.29 (m, 20H), 0.88 (t, J=6.8 Hz, 6H)

MS (m/z): 620.083 (positive ion observation) (Exact Mass: 620.288).

Third Aspect of the Present Invention

Example B-1

The di-Br-substituted DNTT synthesized in Example A-1 was reacted with 1,6-heptadiine by the Sonogashira coupling method to effect polymerization of DNTT.

Specifically, 110 mg (0.15 mmol) of Pd(PPh$_3$)$_2$Cl$_2$ (Mw=701.90), 60 mg (0.31 mmol) of CuI (Mw=190.45) and 170 mg (0.53 mmol) of Cs$_2$CO$_3$ (Mw=325.8) were added to 200 mg (0.41 mmol) of di-Br-substituted DNTT (Mw=498.25), and deaeration under reduced pressure and nitrogen purging were performed five times. Subsequently, 0.14 ml (1.00 mmol) of diisopropylamine (Mw=101.2, d=0.72 g/cm$^3$), 14 ml of dimethylformamide and 0.20 ml (1.70 mmol) of 1,6-heptadiine (Mw=92.14, d=0.81 g/cm$^3$) were added and after again performing deaeration under reduced pressure and nitrogen purging five times, the system was stirred at 120° C. over 12 hours, thereby allowing the reaction to proceed.

By this reaction, a 1,6-heptanediine-bonded dinaphthothienothiophene polymer (structural formula shown below) was obtained. The molecular weight in terms of polystyrene by gel permeation chromatography (GPC) was 5,000 or more (in terms of polystyrene). The solubility of the obtained polymer in chloroform was 0.1 wt % or more. Incidentally, DNTT used as a raw material was substantially not dissolved in chloroform.

[Chem. 64]

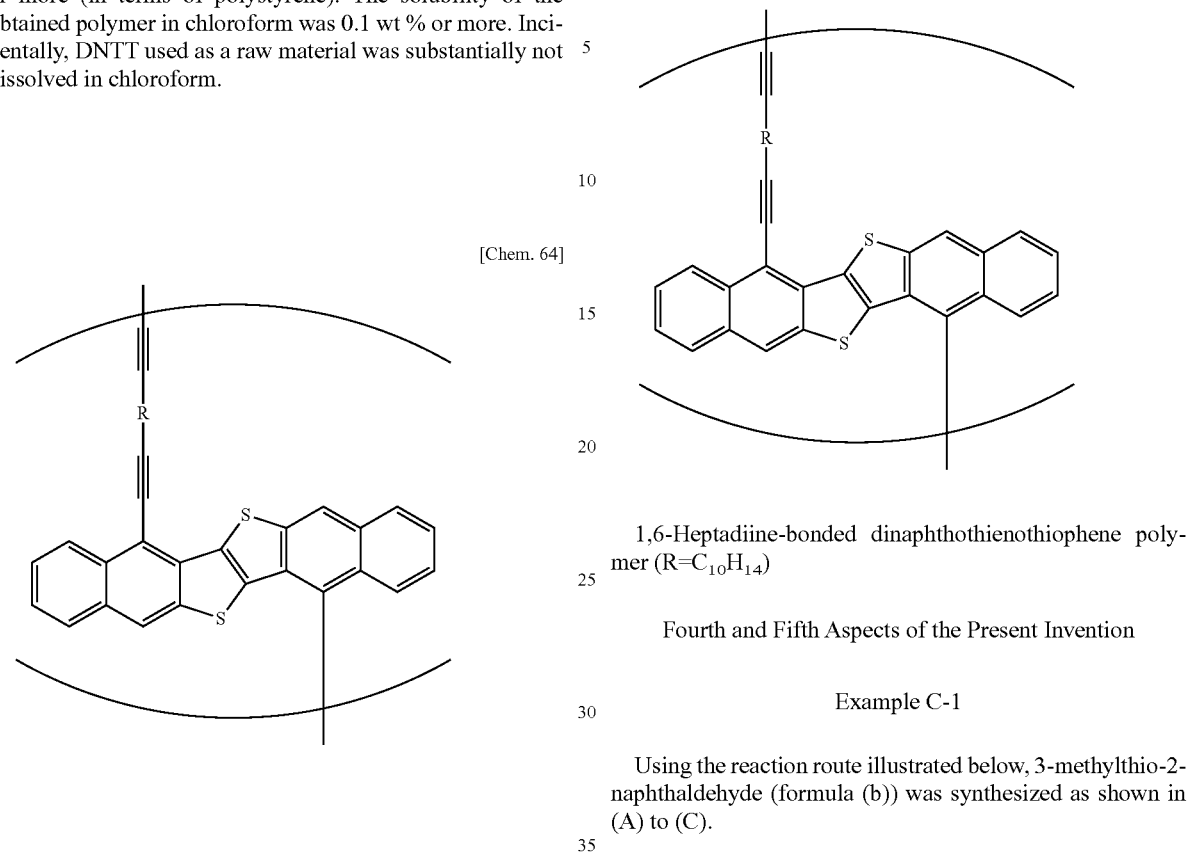

1,6-Heptanediine-bonded dinaphthothienothiophene polymer (R=$C_3H_6$)

Example B-2

The di-Br-substituted DNTT synthesized in Example A-1 was reacted with 1,9-decadiine by the Sonogashira coupling method to effect polymerization of DNTT.

Specifically, 100 mg (0.14 mmol) of Pd(PPh$_3$)$_2$Cl$_2$ (Mw=701.90), 60 mg (0.31 mmol) of CuI (Mw=190.45) and 170 mg (0.53 mmol) of Cs$_2$CO$_3$ (Mw=325.8) were added to 200 mg (0.41 mmol) of di-Br-substituted DNTT (Mw=498.25), and deaeration under pressure and nitrogen purging were performed five times. Subsequently, 0.14 ml (1.00 mmol) of diisopropylamine (Mw=101.2, d=0.72 g/cm$^3$), 14 ml of dimethylformamide, 1 and 0.28 ml (1.70 mmol) of 1,9-decadiine (Mw=134.22, d=0.82 g/cm$^3$) were added and after again performing deaeration under reduced pressure and nitrogen purging five times, the system was stirred at 120° C. over 12 hours, thereby allowing the reaction to proceed.

By this reaction, a 1,9-decadiine-bonded dinaphthothienothiophene polymer (structural formula shown below) was obtained. The molecular weight in terms of polystyrene by gel permeation chromatography (GPC) was 5,000 or more (in terms of polystyrene). The solubility of the obtained polymer in chloroform was 0.1 wt % or more.

[Chem. 65]

1,6-Heptadiine-bonded dinaphthothienothiophene polymer (R=$C_{10}H_{14}$)

Fourth and Fifth Aspects of the Present Invention

Example C-1

Using the reaction route illustrated below, 3-methylthio-2-naphthaldehyde (formula (b)) was synthesized as shown in (A) to (C).

[Chem. 66]

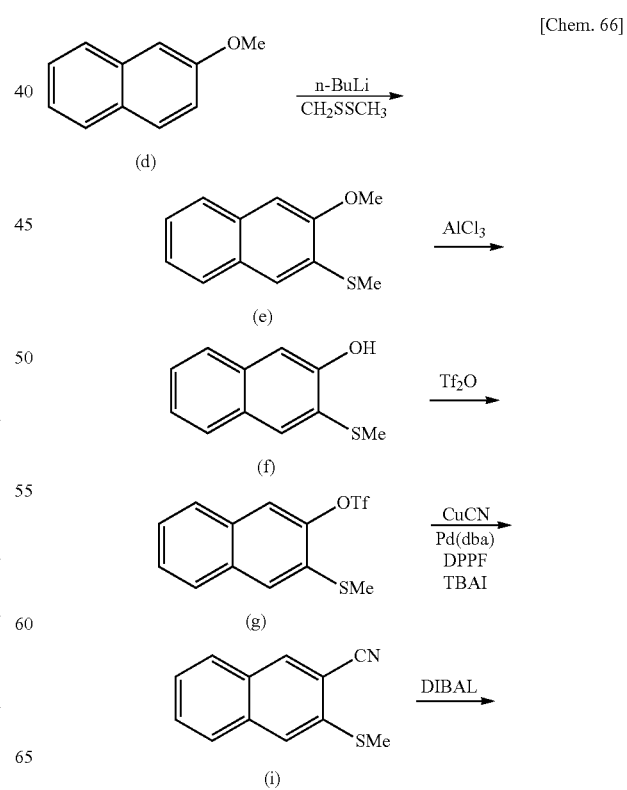

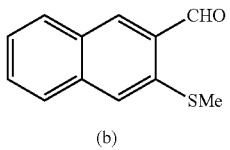

(b)

(A) Synthesis of 3-methylthio-2-naphthyl-trifluoromethanesulfonate

As illustrated below, 3-methylthio-2-naphthyl-trifluoromethanesulfonate (formula (g)) was synthesized from commercially available 2-methoxynaphthalene (formula (d)) by the method described in Non-Patent Document 4.

[Chem. 67]

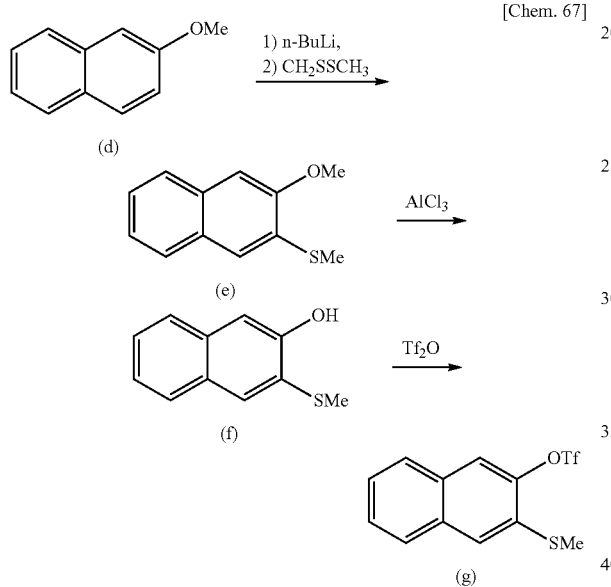

(B) Synthesis of 3-methylthio-2-cyanonaphthalene

As illustrated below, 3-methylthio-2-cyanonaphthalene (formula (I)) was synthesized from 3-methylthio-2-naphthyl-trifluoromethanesulfonate (formula (g)).

[Chem. 68]

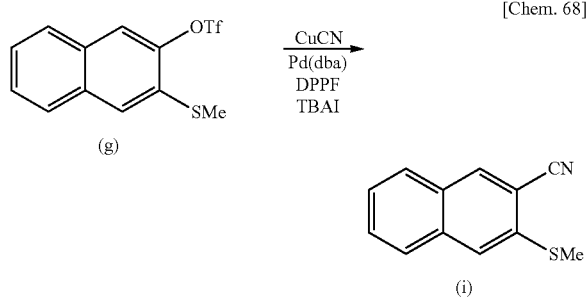

Specifically, 102.2 mg (0.317 mmol) of 3-methylthio-2-naphthyl-trifluoromethanesulfonate (formula (g)) (Mw=322.32), 14.4 mg (0.088 mmol) of 1,1'-bis(diphenylphosphino)ferrocene (DPPF) (Mw=164.32), 9.6 mg (0.014 mmol) of bis(dibenzylideneacetone)palladium (Pd (dba)$_2$) (Mw=701.9), 117.1 mg (0.317 mmol) of tetra-n-butylammonium iodide (TBAI: Mw=369.38) and 90 mg (1.00 mmol) of CuCN were mixed, and nitrogen purging was performed 5 times.

Subsequently, 1.0 ml of dioxane was added, and the system was stirred at 80° C. over 7 hours. After cooling to room temperature, chloroform was added, and a gray solid was removed by filtration. The filtrate was diluted by adding water and hydrochloric acid thereto.

The diluted filtrate was purified twice on a silica gel column by using, as an eluent, a mixed solution of hexane and ethyl acetate (at a ratio of hexane/ethyl acetate=10/1) to obtain 3-methylthio-2-cyanonaphthalene (formula (I)) (Mw=199.27, 27.4 mg, 0.137 mmol, yield: 42.8%).

The $^1$H-NMR results of the obtained 3-methylthio-2-cyanonaphthalene (formula (I)) are shown below.

$^1$H-NMR (500 MHz, CDCl$_3$, 27° C.): δ8.18 (s, 1H), 7.82 (d, J=8.0 Hz, 1H), 7.78 (d, J=8.0 Hz, 1H), 7.66 (s, 1H), 7.61 (dd, J=7.0 Hz, 8.0 Hz, 1H), 7.51 (dd, J=7.0 Hz, 8.0 Hz, 1H), 2.64 (s, 1H).

(C) Synthesis of 3-methylthio-2-naphthaldehyde

As illustrated below, 3-methylthio-2-naphthaldehyde (formula (b)) was synthesized from 3-methylthio-2-cyanonaphthalene (formula (I)).

[Chem. 69]

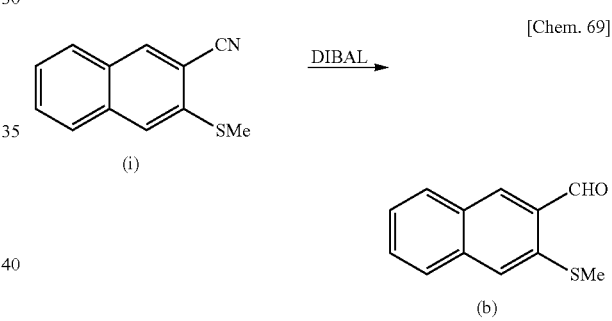

Specifically, to a 30-ml flask, 21.3 mg (0.107 mmol) of 3-methylthio-2-cyanonaphthalene (formula (I)) (Mw=199.27) and 1.0 ml of methylene chloride were added, and the flask was cooled to −78° C. Thereto, 0.1 ml (0.122 mmol) of a hexane solution of diisobutylaluminum hydride (Mw=142.22) was added, and the system was stirred at −70° C. over 30 minutes. Thereafter, 1.0 ml of an aqueous ammonium chloride solution and 1 N hydrochloric acid were added and after extraction with methylene chloride, the solvent was distilled off to obtain 3-methylthio-2-naphthaldehyde (formula (b)) (Mw=207.27) as a yellow oily substance.

The $^1$H-NMR results of the obtained 3-methylthio-2-naphthaldehyde are shown below:

$^1$H-NMR (500 MHz, CDCl$_3$, 27° C.): δ10.3 (s, 1H), 8.31 (s, 1H), 7.92 (d, J=8.0 Hz, 1H), 7.78 (d, J=8.0 Hz, 1H), 7.62-7.59 (m, 1H), 7.60 (s, 1H), 7.49-7.46 (m, 1H), 2.58 (s, 3H).

Example C-2

Using the reaction route illustrated below, 3-methylthio-2-naphthaldehyde (formula (b)) was synthesized as shown in (A) to (D).

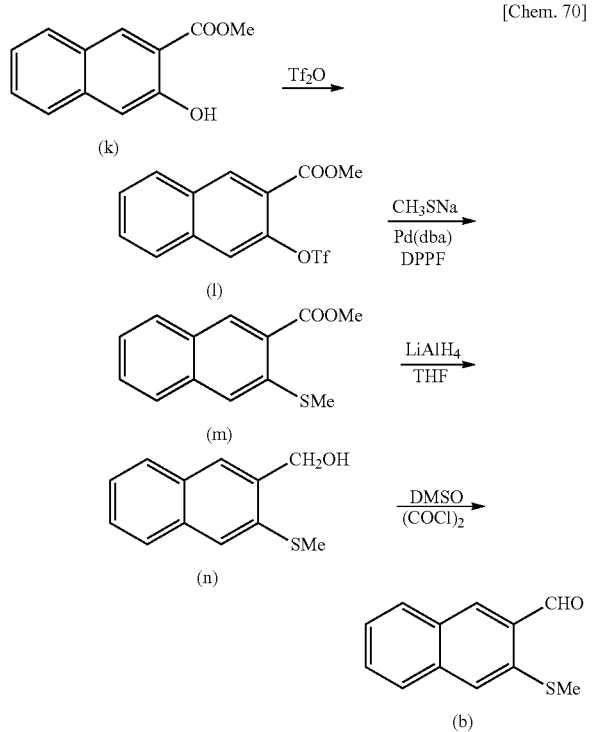

(A) Synthesis of methyl 2-naphthoate-3-trifluoromethanesulfonate

As illustrated below, methyl 2-naphthoate-3-trifluoromethanesulfonate (1) was synthesize from methyl 3-hydroxy-2-naphthoate (k).

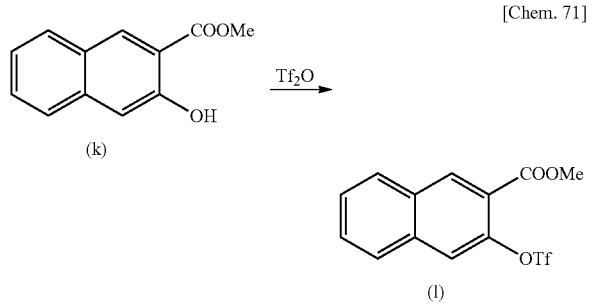

Specifically, a mixture of 2.01 g (10.0 mmol) of methyl 3-hydroxy-2-naphthoate (Mw=199.25), 25 ml of methylene chloride and 2.39 ml (29.67 mmol) of pyridine (Mw=79.10, d=0.98 g/cm³) was cooled to a temperature of 0° C. and stirred.

To the cooled mixed solution, 1.78 ml (10 mmol) of trifluoromethanesulfonic acid anhydride (Tf₂O: Mw=282.14, d=1.72 g/cm³) was added dropwise. After stirring at room temperature over 75 minutes, cold water and 4 N hydrochloric acid were added, and liquid-separation was performed to obtain red oily methyl 2-naphthoate-3-trifluoromethanesulfonate.

The ¹H-NMR results of the obtained methyl 2-naphthoate-3-trifluoromethanesulfonate are shown below:

¹H-NMR (500 MHz, CDCl₃, 50° C.): δ8.66 (s, 1H), 7.99 (d, J=8.5 Hz, 1H), 7.89 (d, J=8.5 Hz, 1H), 7.74 (s, 1H), 7.70-7.67 (m, 1H), 7.65-7.62 (m, 1H) 1.54 (s, 3H).

(B) Synthesis of methyl 3-methylthio-2-naphthoate

As illustrated below, methyl 3-methylthio-2-naphthoate (m) was synthesized from methyl 2-naphthoate-3-trifluoromethanesulfonate (l) obtained in (A) above.

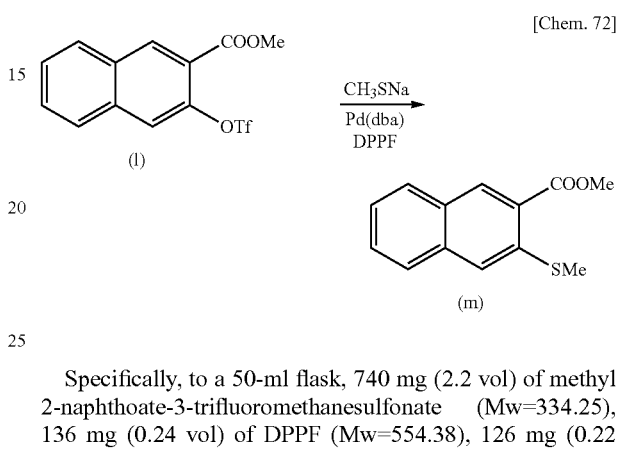

Specifically, to a 50-ml flask, 740 mg (2.2 vol) of methyl 2-naphthoate-3-trifluoromethanesulfonate (Mw=334.25), 136 mg (0.24 vol) of DPPF (Mw=554.38), 126 mg (0.22 μmol) of Pd(dba)₂ (Mw=575.00) and 30 ml of dehydrated toluene were added, and nitrogen purging was performed three times. Thereafter, 433 mg (3.1 vol) of sodium thiomethoxide (CH₃SNa), 6 ml of dehydrated toluene and 6 ml of methanol were added.

Nitrogen purging was performed three times, and then the system was stirred at 85° C. all night. After cooling to room temperature, extraction was performed using ethyl acetate and water. Thereafter, the extractate was subjected to column chromatography using, as an eluent, a mixed solution of chloroform and hexane (chloroform/hexane=7/3) and dried to obtain 142 mg of a solid.

This solid was judged to be the target methyl 3-methylthio-2-naphthoate (formula (m)) from NMR. The yield was 27.6%.

The ¹H-NMR results of the obtained methyl 3-methylthio-2-naphthoate (formula (m)) are shown below: ¹H-NMR (500M Hz, CDCl₃, 27° C.): δ8.54 (s, 1H), 7.85 (d, J=8.5 Hz, 1H), 7.76 (d, J=8.0 Hz, 1H), 7.57 (s, 1H), 7.56 (t, J=8.0 Hz, 1H), 7.44 (t, J=7.5 Hz, 1H), 2.57 (s, 3H) 1.54 (s, 3H).

(C) Synthesis of methanol 3-methylthio-2-naphthoate

As illustrated below, methanol 3-methylthio-2-naphthoate (formula (n)) was synthesized from methyl 3-methylthio-2-naphthoate (formula (m)).

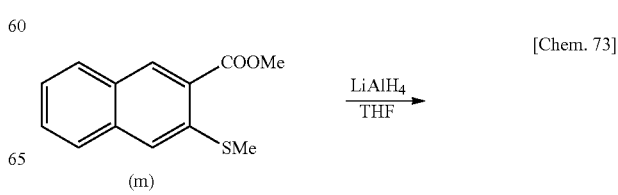

-continued

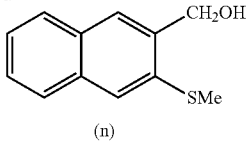

Specifically, 40.1 mg (1.05 mmol) of lithium aluminum hydride (LiAlH₄, Mw=37.95) and 3 ml of tetrahydrofuran (THF) were added and stirred at 0° C. Subsequently, 0.14 g of methyl 3-methylthio-2-naphthoate (Mw=232.30) and 3 ml of THF were added, and the system was stirred at room temperature for 1.5 hours. After cooling to 0° C., filtration and washing twice with saturated brine were performed and then, the solvent was distilled off.

The target 3-methylthio-2-naphthalenemethanol (formula (n)) was obtained as a yellow-white oily substance. the yield was 82.3%.

The ¹H-NMR results of the obtained methanol 3-methylthio-2-naphthoate (formula (n)) are shown below:
¹H-NMR (500 MHz, CDCl₃, 27° C.): δ7.83 (s, 1H), 7.79 (d, J=8.0 Hz, 1H), 7.75 (d, J=8.0 Hz, 1H), 7.61 (s, 1H), 7.48-7.41 (m, 2H), 4.90 (d, J=6.0 Hz, 2H), 2.57 (s, 3H).

(D) Synthesis of 3-methylthio-2-naphthaldehyde

As illustrated below, 3-methylthio-2-naphthaldehyde (b) was synthesized from methanol 3-methylthio-2-naphthoate (n).

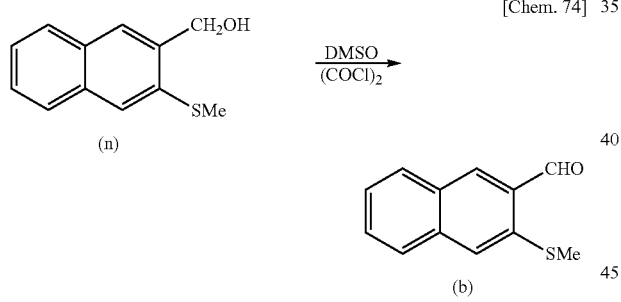

[Chem. 74]

A 30-ml flask was cooled to −80° C., and 0.13 g (1.0 mmol) of oxalyl chloride ((COCl)₂, Mw=126.93, d=1.48 g/cm³), 3.2 ml of methylene chloride and 0.105 g of dimethylsulfoxide (DMSO, Mw=78.13, d=2.66 g/cm³) were added thereto, followed by stirring for 15 minutes. Thereafter, 0.103 g (0.5 mmol) of 3-methylthio-2-naphthalenemethanol (formula (n), Mw=204.29) and 1 ml of methylene chloride were added, and the system was stirred for 15 minutes.

The resulting solution was stirred for 2 hours while gradually raising the temperature, and 0.37 g (3.67 mmol) of triethylamine (Mw=101.19, d=0.73 g/cm³) was added, followed by stirring at 0° C. for 20 minutes. Subsequently, ammonium chloride was added, and extraction with ethyl acetate was performed twice. After drying over magnesium sulfate, the solvent was distilled off.

The crude product was purified on a silica gel column by using hexane/ethyl acetate=8/2 as an eluent to obtain a yellow oily product. NMR revealed that 3-methylthio-2-naphthaldehyde (Mw=202.27) was obtained.

The ¹H-NMR results of the obtained 3-methylthio-2-naphthaldehyde are shown below:
¹H-NMR (500 MHz, CDCl₃, 27° C.): δ10.3 (s, 1H), 8.31 (s, 1H), 7.92 (d, J=8.0 Hz, 1H), 7.78 (d, J=8.0 Hz, 1H), 7.62-7.59 (m, 1H), 7.60 (s, 1H), 7.49-7.46 (m, 1H), 2.58 (s, 3H).

The invention claimed is:
1. A condensed polycyclic aromatic compound represented by the following formula (II):

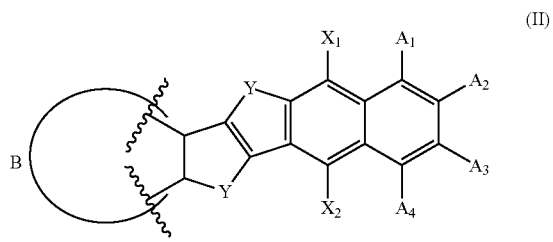

(wherein each of X₁ and X₂ is independently selected from the group consisting of a hydrogen atom, a halogen atom, an alkyl group having from 1 to 20 carbon atoms, an alkenyl group having from 2 to 20 carbon atoms, an alkynyl group having from 2 to 20 carbon atoms, a substituted or unsubstituted aromatic group having from 4 to 20 carbon atoms, a ketone group having from 2 to 10 carbon atoms, an amino group having from 1 to 20 carbon atoms, an amide group having from 1 to 20 carbon atoms, an imide group having from 1 to 20 carbon atoms, a sulfide group having from 1 to 20 carbon atoms, and an alkylsilylalkynyl group having from 1 to 40 carbon atoms, and at least one of X₁ and X₂ is a halogen atom;

B is a condensed ring having at least one benzene ring moiety;

each Y is independently selected from chalcogens; and each of A₁ to A₄ is independently selected from the group consisting of a hydrogen atom, a halogen atom, an alkyl group having from 1 to 20 carbon atoms, an alkenyl group having from 2 to 20 carbon atoms, an alkynyl group having from 2 to 20 carbon atoms, a substituted or unsubstituted aromatic group having from 4 to 20 carbon atoms, a ketone group having from 2 to 10 carbon atoms, an amino group having from 1 to 20 carbon atoms, an amide group having from 1 to 20 carbon atoms, an imide group having from 1 to 20 carbon atoms, a sulfide group having from 1 to 20 carbon atoms, and an alkylsilylalkynyl group having from 1 to 40 carbon atoms, and two adjacent members out of A₁ to A₄ may combine with each other to form a substituted or unsubstituted aromatic group having from 4 to 20 carbon atoms).

2. The compound according to claim 1, which is represented by the following formula (II-1):

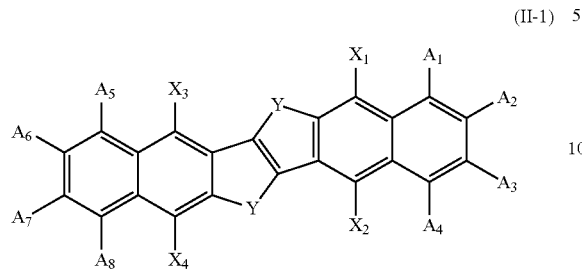

(II-1)

(wherein each of $X_1$ to $X_4$ is independently selected from the group consisting of a hydrogen atom, a halogen atom, an alkyl group having from 1 to 20 carbon atoms, an alkenyl group having from 2 to 20 carbon atoms, an alkynyl group having from 2 to 20 carbon atoms, a substituted or unsubstituted aromatic group having from 4 to 20 carbon atoms, a ketone group having from 2 to 10 carbon atoms, an amino group having from 1 to 20 carbon atoms, an amide group having from 1 to 20 carbon atoms, an imide group having from 1 to 20 carbon atoms, a sulfide group having from 1 to 20 carbon atoms, and an alkylsilylalkynyl group having from 1 to 40 carbon atoms, and at least one of $X_1$ to $X_4$ is a halogen atom;

each Y is independently selected from chalcogens; and each of $A_1$ to $A_8$ is independently selected from the group consisting of a hydrogen atom, a halogen atom, an alkyl group having from 1 to 20 carbon atoms, an alkenyl group having from 2 to 20 carbon atoms, an alkynyl group having from 2 to 20 carbon atoms, a substituted or unsubstituted aromatic group having from 4 to 20 carbon atoms, a ketone group having from 2 to 10 carbon atoms, an amino group having from 1 to 20 carbon atoms, an amide group having from 1 to 20 carbon atoms, an imide group having from 1 to 20 carbon atoms, a sulfide group having from 1 to 20 carbon atoms, and an alkylsilylalkynyl group having from 1 to 40 carbon atoms, and two adjacent members out of $A_1$ to $A_8$ may combine with each other to form a substituted or unsubstituted aromatic group having from 4 to 20 carbon atoms).

3. The compound according to claim 2, wherein each of $X_2$ and $X_3$ is independently selected from the group consisting of a hydrogen atom, a halogen atom, an alkyl group having from 1 to 20 carbon atoms, an alkenyl group having from 2 to 20 carbon atoms, an alkynyl group having from 2 to 20 carbon atoms, a substituted or unsubstituted aromatic group having from 4 to 20 carbon atoms, a ketone group having from 2 to 10 carbon atoms, an amino group having from 1 to 20 carbon atoms, an amide group having from 1 to 20 carbon atoms, an imide group having from 1 to 20 carbon atoms, a sulfide group having from 1 to 20 carbon atoms, and an alkylsilylalkynyl group having from 1 to 40 carbon atoms, at least one of $X_2$ and $X_3$ is a halogen atom, and $X_1$ and $X_4$ are a hydrogen atom.

4. The compound according to claim 2, which is represented by the following formula (II-1-1):

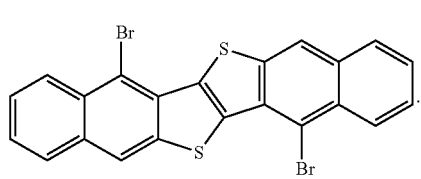

(II-1-1)

5. The compound according to claim 2, which is represented by the following formula (II-1-2):

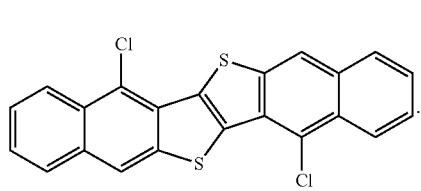

(II-1-2)

6. The compound according to claim 1, which is represented by the following formula (II-2):

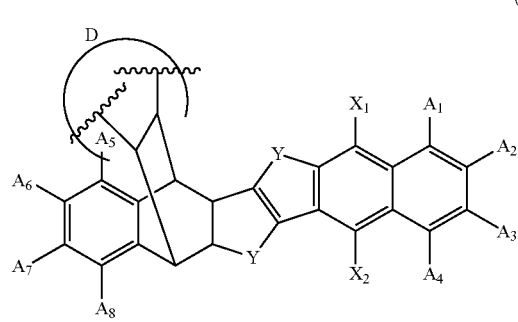

(II-2)

(wherein each of $X_1$ and $X_2$ is independently selected from the group consisting of a hydrogen atom, a halogen atom, an alkyl group having from 1 to 20 carbon atoms, an alkenyl group having from 2 to 20 carbon atoms, an alkynyl group having from 2 to 20 carbon atoms, a substituted or unsubstituted aromatic group having from 4 to 20 carbon atoms, a ketone group having from 2 to 10 carbon atoms, an amino group having from 1 to 20 carbon atoms, an amide group having from 1 to 20 carbon atoms, an imide group having from 1 to 20 carbon atoms, a sulfide group having from 1 to 20 carbon atoms, and an alkylsilylalkynyl group having from 1 to 40 carbon atoms, and at least one of $X_1$ and $X_2$ is a halogen atom;

D is a substituent having from 2 to 20 carbon atoms, which is obtained by adding a dienophilic alkene to a benzene ring;

each Y is independently selected from chalcogens; and each of $A_1$ to $A_8$ is independently selected from the group consisting of a hydrogen atom, a halogen atom, an alkyl group having from 1 to 20 carbon atoms, an alkenyl group having from 2 to 20 carbon atoms, an alkynyl group having from 2 to 20 carbon atoms, a substituted or unsubstituted aromatic group having from 4 to 20 carbon atoms, a ketone group having from 2 to 10 carbon atoms, an amino group having from 1 to 20 carbon atoms, an amide group having from 1 to 20 carbon atoms, an imide group having from 1 to 20 carbon atoms, a sulfide group having from 1 to 20 carbon atoms, and an alkylsilylalkynyl group having from 1 to 40 carbon atoms, and two adjacent members out of $A_1$ to $A_8$ may combine with each other to form a substituted or unsubstituted aromatic group having from 4 to 20 carbon atoms).

7. The compound according to claim 6, wherein both $X_1$ and $X_2$ are a halogen atom.

8. The compound according to claim 6, which is represented by the following formula (II-2-1):

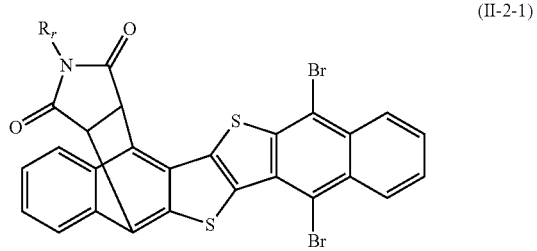

(II-2-1)

(wherein each $R_r$ is independently selected from the group consisting of hydrogen, a halogen, a hydroxyl group, an amide group, a mercapto group, a cyano group, an alkyl group having from 1 to 10 carbon atoms, an alkenyl group having from 2 to 10 carbon atoms, an alkynyl group having from 2 to 10 carbon atoms, an alkoxy group having from 1 to 10 carbon atoms, a substituted or unsubstituted aromatic group having from 4 to 10 carbon atoms, an ester group having from 1 to 10 carbon atoms, an ether group having from 1 to 10 carbon atoms, a ketone group having from 1 to 10 carbon atoms, an amino group having from 1 to 10 carbon atoms, an amide group having from 1 to 10 carbon atoms, an imide group having from 1 to 10 carbon atoms, and a sulfide group having from 1 to 10 carbon atoms).

9. A method for synthesizing the condensed polycyclic aromatic compound of claim 1, comprising:
(a) providing a composition containing an organic solvent and a condensed polycyclic aromatic compound represented by the following formula (III):

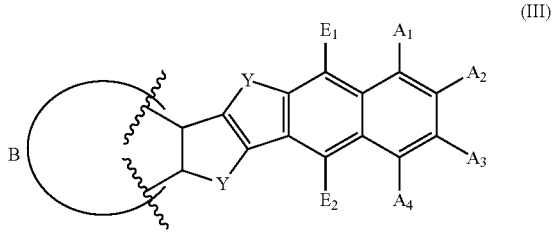

(III)

(wherein each of $E_1$ and $E_2$ is independently selected from the group consisting of a hydrogen atom, a halogen atom, an alkyl group having from 1 to 20 carbon atoms, an alkenyl group having from 2 to 20 carbon atoms, an alkynyl group having from 2 to 20 carbon atoms, a substituted or unsubstituted aromatic group having from 4 to 20 carbon atoms, a ketone group having from 2 to 10 carbon atoms, an amino group having from 1 to 20 carbon atoms, an amide group having from 1 to 20 carbon atoms, an imide group having from 1 to 20 carbon atoms, a sulfide group having from 1 to 20 carbon atoms, and an alkylsilylalkynyl group having from 1 to 40 carbon atoms, and at least one of $E_1$ and $E_2$ is a hydrogen atom;

B is a condensed ring having at least one benzene ring moiety;

each Y is independently selected from chalcogens; and each of $A_1$ to $A_4$ is independently selected from the group consisting of a hydrogen atom, a halogen atom, an alkyl group having from 1 to 20 carbon atoms, an alkenyl group having from 2 to 20 carbon atoms, an alkynyl group having from 2 to 20 carbon atoms, a substituted or unsubstituted aromatic group having from 4 to 20 carbon atoms, a ketone group having from 2 to 10 carbon atoms, an amino group having from 1 to 20 carbon atoms, an amide group having from 1 to 20 carbon atoms, an imide group having from 1 to 20 carbon atoms, a sulfide group having from 1 to 20 carbon atoms, and an alkylsilylalkynyl group having from 1 to 40 carbon atoms, and two adjacent members out of $A_1$ to $A_4$ may combine with each other to form a substituted or unsubstituted aromatic group having from 4 to 20 carbon atoms), and (b) adding a halogen to said composition.

10. The method according to claim 9, wherein said compound of formula (III) is represented by the following formula (III-1):

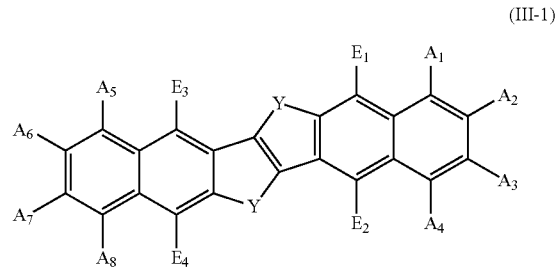

(III-1)

(wherein each of $E_1$ to $E_4$ is independently selected from the group consisting of a hydrogen atom, a halogen atom, an alkyl group having from 1 to 20 carbon atoms, an alkenyl group having from 2 to 20 carbon atoms, an alkynyl group having from 2 to 20 carbon atoms, a substituted or unsubstituted aromatic group having from 4 to 20 carbon atoms, a ketone group having from 2 to 10 carbon atoms, an amino group having from 1 to 20 carbon atoms, an amide group having from 1 to 20 carbon atoms, an imide group having from 1 to 20 carbon atoms, a sulfide group having from 1 to 20 carbon atoms, and an alkylsilylalkynyl group having from 1 to 40 carbon atoms, and at least one of $E_1$ to $E_4$ is a hydrogen atom;

each Y is independently selected from chalcogens; and each of $A_1$ to $A_8$ is independently selected from the group consisting of a hydrogen atom, a halogen atom, an alkyl group having from 1 to 20 carbon atoms, an alkenyl group having from 2 to 20 carbon atoms, an alkynyl group having from 2 to 20 carbon atoms, a substituted or unsubstituted aromatic group having from 4 to 20 carbon atoms, a ketone group having from 2 to 10 carbon atoms, an amino group having from 1 to 20 carbon atoms, an amide group having from 1 to 20 carbon atoms, an imide group having from 1 to 20 carbon atoms, a sulfide group having from 1 to 20 carbon atoms, and an alkylsilylalkynyl group having from 1 to 40 carbon atoms, and two adjacent members out of $A_1$ to $A_8$ may combine with each other to form a substituted or unsubstituted aromatic group having from 4 to 20 carbon atoms).

11. The method according to claim 10, wherein all of $E_1$ to $E_4$ are a hydrogen atom.

12. The method according to claim 10, wherein said compound of formula (III-1) is represented by the following formula (III-1-1):

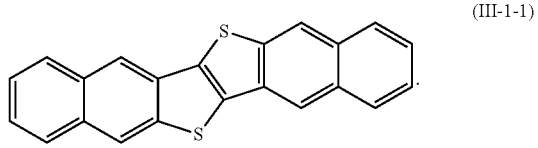 [SMILES: c1ccc2cc3c(cc2c1)sc1c2cc4ccccc4cc2sc31]

(III-1-1)

13. The method according to claim 9, wherein said compound of formula (III) is represented by the following formula (III-2):

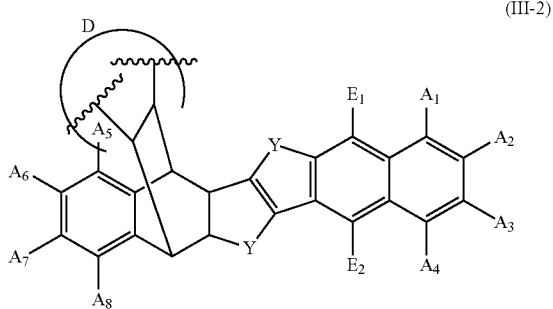

(III-2)

(wherein each of $E_1$ and $E_2$ is independently selected from the group consisting of a hydrogen atom, a halogen atom, an alkyl group having from 1 to 20 carbon atoms, an alkenyl group having from 2 to 20 carbon atoms, an alkynyl group having from 2 to 20 carbon atoms, a substituted or unsubstituted aromatic group having from 4 to 20 carbon atoms, a ketone group having from 2 to 10 carbon atoms, an amino group having from 1 to 20 carbon atoms, an amide group having from 1 to 20 carbon atoms, an imide group having from 1 to 20 carbon atoms, a sulfide group having from 1 to 20 carbon atoms, and an alkylsilylalkynyl group having from 1 to 40 carbon atoms, and at least one of $E_1$ and $E_2$ is a hydrogen atom;

D is a substituent having from 2 to 20 carbon atoms, which is obtained by adding a dienophilic alkene to a benzene ring;

each Y is independently selected from chalcogens; and each of $A_1$ to $A_g$ is independently selected from the group consisting of a hydrogen atom, a halogen atom, an alkyl group having from 1 to 20 carbon atoms, an alkenyl group having from 2 to 20 carbon atoms, an alkynyl group having from 2 to 20 carbon atoms, a substituted or unsubstituted aromatic group having from 4 to 20 carbon atoms, a ketone group having from 2 to 10 carbon atoms, an amino group having from 1 to 20 carbon atoms, an amide group having from 1 to 20 carbon atoms, an imide group having from 1 to 20 carbon atoms, a sulfide group having from 1 to 20 carbon atoms, and an alkylsilylalkynyl group having from 1 to 40 carbon atoms, and two adjacent members out of $A_1$ to $A_g$ may combine with each other to form a substituted or unsubstituted aromatic group having from 4 to 20 carbon atoms).

14. The method according to claim 13, wherein both $E_1$ and $E_3$ are hydrogen.

15. The method according to claim 13, wherein said compound of formula (III-2) is represented by the following formula (III-2-1):

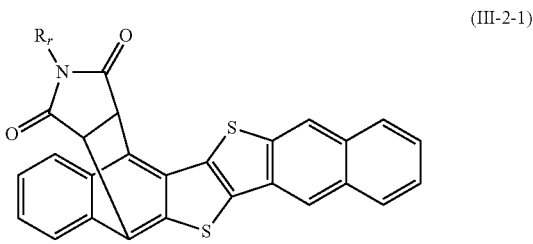

(III-2-1)

(wherein each $R_r$ is independently selected from the group consisting of hydrogen, a halogen, a hydroxyl group, an amide group, a mercapto group, a cyano group, an alkyl group having from 1 to 10 carbon atoms, an alkenyl group having from 2 to 10 carbon atoms, an alkynyl group having from 2 to 10 carbon atoms, an alkoxy group having from 1 to 10 carbon atoms, a substituted or unsubstituted aromatic group having from 4 to 10 carbon atoms, an ester group having from 1 to 10 carbon atoms, an ether group having from 1 to 10 carbon atoms, a ketone group having from 1 to 10 carbon atoms, an amino group having from 1 to 10 carbon atoms, an amide group having from 1 to 10 carbon atoms, an imide group having from 1 to 10 carbon atoms, and a sulfide group having from 1 to 10 carbon atoms).

16. A method for synthesizing a condensed polycyclic aromatic compound represented by the following formula (I), comprising:

(a) providing a composition containing an organic solvent and the compound of claim 14, and (b) substituting at least one halogen atom out of $X_1$ to $X_4$ with a substituent selected from the group consisting of an alkyl group having from 1 to 20 carbon atoms, an alkenyl group having from 2 to 20 carbon atoms, an alkynyl group having from 2 to 20 carbon atoms, a substituted or unsubstituted aromatic group having from 4 to 20 carbon atoms, and an alkylsilylalkynyl group having from 1 to 40 carbon atoms:

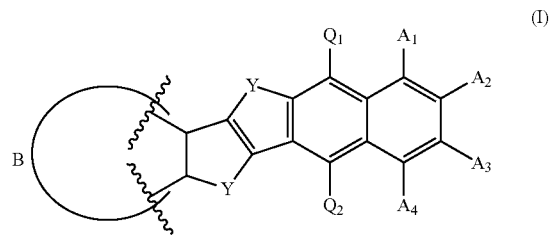

(I)

(wherein each of $Q_1$ and $Q_2$ is independently selected from the group consisting of a hydrogen atom, a halogen atom, an alkyl group having from 1 to 20 carbon atoms, an alkenyl group having from 2 to 20 carbon atoms, an alkynyl group having from 2 to 20 carbon atoms, a substituted or unsubstituted aromatic group having from 4 to 20 carbon atoms, and an alkylsilylalkynyl group having from 1 to 40 carbon atoms, and at least one of $Q_1$ and $Q_2$ is a group other than a hydrogen atom and a halogen atom;

B is a substituted or unsubstituted condensed ring having at least one benzene ring moiety;

each Y is independently selected from chalcogens; and each of $A_1$ to $A_4$ is independently selected from the group consisting of a hydrogen atom, a halogen atom, an alkyl group having from 1 to 20 carbon atoms, an alkenyl group having from 2 to 20 carbon atoms, an alkynyl group having from 2 to 20 carbon atoms, a substituted or unsubstituted aromatic group having from 4 to 20 carbon atoms, a ketone group having from 2 to 10 carbon atoms, an amino group having from 1 to 20 carbon atoms, an amide group having from 1 to 20 carbon atoms, an imide group having from 1 to 20 carbon atoms, a sulfide group having from 1 to 20 carbon atoms, and an alkylsilylalkynyl group having from 1 to 40 carbon atoms, and two adjacent members out of $A_1$ to $A_4$ may combine with each other to form a substituted or unsubstituted aromatic group having from 4 to 20 carbon atoms).

* * * * *